(12) United States Patent
Freese et al.

(10) Patent No.: US 8,941,046 B2
(45) Date of Patent: Jan. 27, 2015

(54) METHODS AND DEVICES FOR OPTICALLY DETERMINING A CHARACTERISTIC OF A SUBSTANCE

(75) Inventors: Robert Freese, Pittsboro, NC (US); Christopher Michael Jones, Houston, TX (US); David Perkins, The Woodlands, TX (US); Michael Simcock, Columbia, SC (US); William Soltmann, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 182 days.

(21) Appl. No.: 13/456,350

(22) Filed: Apr. 26, 2012

(65) Prior Publication Data

US 2013/0284899 A1    Oct. 31, 2013

(51) Int. Cl.
| | | |
|---|---|---|
| *G01N 21/25* | (2006.01) | |
| *G01N 21/17* | (2006.01) | |
| *G01N 21/27* | (2006.01) | |
| *G01N 21/31* | (2006.01) | |
| *G06E 3/00* | (2006.01) | |
| *G01J 3/12* | (2006.01) | |

(52) U.S. Cl.
CPC .............. *G01N 21/17* (2013.01); *G01N 21/274* (2013.01); *G01N 21/31* (2013.01); *G06E 3/001* (2013.01); *G01J 2003/1226* (2013.01); *G01N 2021/3137* (2013.01); *G01N 2021/3174* (2013.01)
USPC .......... 250/208.2; 356/419; 356/310; 356/330

(58) Field of Classification Search
USPC .......... 250/208.2; 356/51, 300, 303, 417, 318
See application file for complete search history.

(56) References Cited

U.S. PATENT DOCUMENTS

| | | | |
|---|---|---|---|
| 3,488,491 | A | 1/1970 | Schuman |
| 4,761,073 | A | 8/1988 | Meltz et al. |
| 4,795,262 | A | 1/1989 | Morris et al. |
| 4,806,012 | A | 2/1989 | Meltz et al. |
| 4,882,492 | A | 11/1989 | Schlager |

(Continued)

FOREIGN PATENT DOCUMENTS

| | | |
|---|---|---|
| EP | 1061355 A1 | 12/2000 |
| EP | 1969326 | 9/2008 |

(Continued)

OTHER PUBLICATIONS

Qu et al, "Fluorescence Spectral Imaging for Characterization of Tissue Based on Multivariate Statistical Analysis," Journal of the Optical Society of America, vol. 19, No. 9, 2002 XP055046065.

(Continued)

*Primary Examiner* — Tony Ko
(74) *Attorney, Agent, or Firm* — McDermott Will & Emery LLP; Craig W. Roddy

(57) ABSTRACT

Optical computing devices are disclosed. One exemplary optical computing device includes an electromagnetic radiation source configured to optically interact with a sample and first and second integrated computational elements arranged in primary and reference channels, respectively. The first and second integrated computational elements produce first and second modified electromagnetic radiations, and a detector is arranged to receive the first and second modified electromagnetic radiations and generate an output signal corresponding to the characteristic of the sample.

23 Claims, 6 Drawing Sheets

(56) References Cited

U.S. PATENT DOCUMENTS

| | | | |
|---|---|---|---|
| 5,399,854 A | 3/1995 | Dunphy et al. |
| 5,426,506 A | 6/1995 | Ellingson et al. |
| 5,493,390 A | 2/1996 | Varasi et al. |
| 5,737,076 A | 4/1998 | Glaus et al. |
| 6,091,504 A | 7/2000 | Walker et al. |
| 6,198,531 B1 | 3/2001 | Myrick et al. |
| 6,529,276 B1 * | 3/2003 | Myrick .......................... 356/419 |
| 6,576,188 B1 | 6/2003 | Rose et al. |
| 7,123,844 B2 | 10/2006 | Myrick |
| 7,138,156 B1 | 11/2006 | Myrick et al. |
| 7,332,094 B2 | 2/2008 | Abney et al. |
| 7,472,748 B2 | 1/2009 | Gdanski et al. |
| 7,623,233 B2 | 11/2009 | Freese et al. |
| 7,697,141 B2 | 4/2010 | Jones et al. |
| 7,712,527 B2 | 5/2010 | Roddy |
| 7,834,999 B2 | 11/2010 | Myrick et al. |
| 7,911,605 B2 | 3/2011 | Myrick et al. |
| 7,920,258 B2 | 4/2011 | Myrick et al. |
| 7,934,556 B2 | 5/2011 | Clark et al. |
| 8,141,633 B2 | 3/2012 | Hampton et al. |
| 8,253,619 B2 | 8/2012 | Holbrook et al. |
| 8,345,243 B2 | 1/2013 | Ghinovker et al. |
| 8,547,556 B2 | 10/2013 | Irani |
| 8,780,352 B2 | 7/2014 | Freese et al. |
| 2001/0020675 A1 | 9/2001 | Tubel et al. |
| 2002/0023752 A1 | 2/2002 | Qu et al. |
| 2002/0071121 A1 | 6/2002 | Ortyn et al. |
| 2002/0109080 A1 | 8/2002 | Tubel et al. |
| 2003/0056581 A1 | 3/2003 | Turner et al. |
| 2003/0145988 A1 | 8/2003 | Mullins et al. |
| 2004/0045705 A1 | 3/2004 | Gardner et al. |
| 2004/0129884 A1 | 7/2004 | Boyle et al. |
| 2006/0102343 A1 | 5/2006 | Skinner et al. |
| 2006/0142955 A1 | 6/2006 | Jones et al. |
| 2006/0183183 A1 | 8/2006 | Felkner et al. |
| 2007/0248488 A1 | 10/2007 | Denkewicz |
| 2007/0282647 A1 | 12/2007 | Freese et al. |
| 2008/0041594 A1 | 2/2008 | Boles et al. |
| 2008/0133193 A1 | 6/2008 | Gdanski et al. |
| 2008/0231849 A1 | 9/2008 | Myrick et al. |
| 2008/0276687 A1 | 11/2008 | Myrick et al. |
| 2009/0002697 A1 | 1/2009 | Freese et al. |
| 2009/0015819 A1 | 1/2009 | Van Beek et al. |
| 2009/0033933 A1 | 2/2009 | Myrick et al. |
| 2009/0073433 A1 | 3/2009 | Myrick et al. |
| 2009/0087912 A1 | 4/2009 | Ramos et al. |
| 2009/0097024 A1 | 4/2009 | Blackburn et al. |
| 2009/0137887 A1 | 5/2009 | Shariati et al. |
| 2009/0140144 A1 | 6/2009 | Myrick et al. |
| 2009/0154288 A1 | 6/2009 | Heathman |
| 2009/0182693 A1 | 7/2009 | Fulton et al. |
| 2009/0205821 A1 | 8/2009 | Smith |
| 2009/0213380 A1 | 8/2009 | Appel et al. |
| 2009/0216504 A1 | 8/2009 | Priore et al. |
| 2009/0219512 A1 | 9/2009 | Myrick et al. |
| 2009/0219538 A1 | 9/2009 | Myrick et al. |
| 2009/0219539 A1 | 9/2009 | Myrick et al. |
| 2009/0250613 A1 | 10/2009 | Myrick et al. |
| 2009/0299946 A1 | 12/2009 | Myrick et al. |
| 2009/0305330 A1 | 12/2009 | Kroon et al. |
| 2009/0316150 A1 | 12/2009 | Myrick et al. |
| 2010/0006292 A1 | 1/2010 | Boles et al. |
| 2010/0027014 A1 | 2/2010 | Hart et al. |
| 2010/0042348 A1 | 2/2010 | Bakker |
| 2010/0050905 A1 | 3/2010 | Lewis et al. |
| 2010/0051266 A1 | 3/2010 | Roddy et al. |
| 2010/0051275 A1 | 3/2010 | Lewis et al. |
| 2010/0073666 A1 | 3/2010 | Perkins et al. |
| 2010/0084132 A1 | 4/2010 | Noya et al. |
| 2010/0141952 A1 | 6/2010 | Myrick et al. |
| 2010/0148785 A1 | 6/2010 | Schaefer et al. |
| 2010/0149523 A1 | 6/2010 | Heideman et al. |
| 2010/0149537 A1 | 6/2010 | Myrick et al. |
| 2010/0153048 A1 | 6/2010 | Myrick et al. |
| 2010/0182600 A1 | 7/2010 | Freese et al. |
| 2010/0195105 A1 | 8/2010 | Myrick et al. |
| 2010/0245096 A1 | 9/2010 | Jones et al. |
| 2010/0265509 A1 | 10/2010 | Jones et al. |
| 2010/0302539 A1 | 12/2010 | Myrick et al. |
| 2010/0305741 A1 | 12/2010 | Myrick |
| 2010/0326659 A1 | 12/2010 | Schultz et al. |
| 2010/0328669 A1 | 12/2010 | Myrick et al. |
| 2011/0048708 A1 | 3/2011 | Glasbergen et al. |
| 2011/0163046 A1 | 7/2011 | Neal et al. |
| 2011/0199610 A1 | 8/2011 | Myrick et al. |
| 2012/0187283 A1 | 7/2012 | Yamada et al. |
| 2012/0211650 A1 | 8/2012 | Jones et al. |
| 2012/0250017 A1 | 10/2012 | Morys et al. |
| 2013/0031970 A1 | 2/2013 | Freese et al. |
| 2013/0031971 A1 | 2/2013 | Freese et al. |
| 2013/0031972 A1 | 2/2013 | Freese et al. |
| 2013/0032333 A1 | 2/2013 | Freese et al. |
| 2013/0032340 A1 | 2/2013 | Freese et al. |
| 2013/0034842 A1 | 2/2013 | Tunheim et al. |
| 2013/0284894 A1 | 10/2013 | Freese et al. |
| 2013/0284895 A1 | 10/2013 | Freese et al. |
| 2013/0284896 A1 | 10/2013 | Freese et al. |
| 2013/0284897 A1 | 10/2013 | Freese et al. |
| 2013/0284898 A1 | 10/2013 | Freese et al. |
| 2013/0284900 A1 | 10/2013 | Freese et al. |
| 2013/0284901 A1 | 10/2013 | Freese et al. |
| 2013/0284904 A1 | 10/2013 | Freese et al. |
| 2013/0286398 A1 | 10/2013 | Freese et al. |
| 2013/0286399 A1 | 10/2013 | Freese et al. |
| 2013/0287061 A1 | 10/2013 | Freese et al. |
| 2014/0263974 A1 | 9/2014 | Freese et al. |
| 2014/0306096 A1 | 10/2014 | Freese et al. |

FOREIGN PATENT DOCUMENTS

| | | |
|---|---|---|
| EP | 2087328 | 8/2009 |
| EP | 2140238 | 1/2010 |
| EP | 2169384 A1 | 3/2010 |
| EP | 2320027 A1 | 5/2011 |
| GB | 2353310 A | 2/2001 |
| WO | 2004018840 A1 | 3/2004 |
| WO | 2004057285 A1 | 7/2004 |
| WO | 2005064314 A1 | 7/2005 |
| WO | 2006021928 A1 | 3/2006 |
| WO | 2006110041 A1 | 10/2006 |
| WO | 2006114773 A1 | 11/2006 |
| WO | 2006137902 | 12/2006 |
| WO | 2007064575 | 6/2007 |
| WO | 2007098392 A2 | 8/2007 |
| WO | 2008057912 A2 | 5/2008 |
| WO | 2008057913 A2 | 5/2008 |
| WO | 2011063086 A1 | 5/2011 |
| WO | 2013162744 A1 | 10/2013 |
| WO | 2013162787 A1 | 10/2013 |
| WO | 2013162795 A1 | 10/2013 |
| WO | 2013162799 A1 | 10/2013 |
| WO | 2013162809 A1 | 10/2013 |
| WO | 2013162860 A1 | 10/2013 |
| WO | 2013162861 A1 | 10/2013 |
| WO | 2013162901 A1 | 10/2013 |
| WO | 2013162906 A1 | 10/2013 |
| WO | 2013162913 A1 | 10/2013 |
| WO | 2013162914 A1 | 10/2013 |

OTHER PUBLICATIONS

International Search Report and Written Opinion for PCT/US2013/036287 dated Aug. 2, 2013.

International Search Report and Written Opinion for PCT/US2013/036294 dated Aug. 7, 2013.

Myrick, et al. "Spectral Tolerance Determination for Multivariate Optical Element Design," Fresenuis' Journal of Analytical Chemistry, 369:2001; pp. 351-355.

Gdanski et al., "A New Model for Matching Fracturing Fluid Flowback Composition," 2007 SPE Hydraulic Fracturing Technology Conference held in College Station, Texas, SPE 106040.

Gdanski et al., "Using Lines-of-Solutions to Understand Fracture Conductivity and Fracture Cleanup," SPE Production and Operations Symposium held in Oklahoma City, OK, 2011, SPE 142096.

(56) References Cited

OTHER PUBLICATIONS

Myrick et al., "Application of Multivariate Optical Computing to Simple Near-Infrared Point Measurements," Proceedings of SPIE, US, vol. 4574, 2002, pp. 208-215, XP002391230.

Nelson et al., "Multivariate Optical Computation for Predictive Spectroscopy," Analytical Chemistry, vol. 70, No. 1, 1998, pp. 73-82, XP055067630.

Bialkowski, "Species Discrimination and Quantitative Estimation Using Incoherent Linear Optical Signal Processing of Emission Signals," Analytical Chemistry, vol. 58, No. 12, 1986, pp. 2561-2563, XP055067237.

Medendorp, et al., "Applications of Interated Sensing and Processing in Spectroscopic Imaging and Sensing," Journal of Chemometrics, vol. 19, No. 10, 2006, pp. 533-542, XP055067235.

Bin Dai et al., "Molecular Factor Computing for Predictive Spectroscopy," Pharmaceutical Research, Kluwer Academic Publishers-Plenum Publishers, NL, vol. 24, No. 8, 2007, pp. 1441-1449, XP019507244.

International Search Report and Written Opinion for PCT/US2013/036177 dated Jun. 28, 2013.

International Search Report and Written Opinion for PCT/US2013/036107 dated Jun. 28, 2013.

International Search Report and Written Opinion for PCT/US2013/033975 dated Jun. 28, 2013.

International Search Report and Written Opinion for PCT/US2013/035572 dated Jun. 28, 2013.

International Search Report and Written Opinion for PCT/US2013035604 dated Jun. 28, 2013.

International Search Report and Written Opinion for PCT/US2013/031467 dated Jun. 28, 2013.

International Search Report and Writen Opinion for PCT/US2013/031960 dated Jun. 28, 2013.

International Search Report and Written Opinion for PCT/US2013/032970 dated Jun. 28, 2013.

International Search Report and Written Opinion for PCT/US2013/033256 dated Jun. 28, 2013.

International Search Report and Written Opinion for PCT/US2013/033502 dated Jun. 28, 2013.

Sullivan et al. "Implementation of a Numerical Needle Method for Thin-Film Design," Applied Optics, vol. 35, No. 28, pp. 5484-5492, 1996.

Dobrowolski et al., "Refinement of Optical Multilayer Systems with Different Optimization Procedures," Applied Optics, vol. 29, No. 19, pp. 2876-2893, 1990.

Halliburton Brochure for "Acid-on-the-Fly (AOF) Blending System," published 2009.

Official Action for Canadian Patent Application No. 2,842,703 dated Jul. 25, 2014.

\* cited by examiner

METHODS AND DEVICES FOR OPTICALLY DETERMINING A CHARACTERISTIC OF A SUBSTANCE

BACKGROUND

The present invention generally relates to systems and methods of optical computing and, more specifically, to systems and methods of determining a particular characteristic of a substance using two or more integrated computational elements.

Spectroscopic techniques for measuring various characteristics of materials are well known and are routinely used under laboratory conditions. In some cases, these spectroscopic techniques can be carried out without using an involved sample preparation. It is more common, however, to carry out various sample preparation steps before conducting the analysis. Reasons for conducting sample preparation steps can include, for example, removing interfering background materials from the analyte of interest, converting the analyte of interest into a chemical form that can be better detected by the chosen spectroscopic technique, and adding standards to improve the accuracy of quantitative measurements. Thus, there is usually a delay in obtaining an analysis due to sample preparation time, even discounting the transit time of transporting the sample to a laboratory.

Although spectroscopic techniques can, at least in principle, be conducted at a job site or in a process, the foregoing concerns regarding sample preparation times can still apply. Furthermore, the transitioning of spectroscopic instruments from a laboratory into a field or process environment can be expensive and complex. Reasons for these issues can include, for example, the need to overcome inconsistent temperature, humidity, and vibration encountered during field or process use. Furthermore, sample preparation, when required, can be difficult under field analysis conditions. The difficulty of performing sample preparation in the field can be especially problematic in the presence of interfering materials, which can further complicate conventional spectroscopic analyses. Quantitative spectroscopic measurements can be particularly challenging in both field and laboratory settings due to the need for precision and accuracy in sample preparation and spectral interpretation.

SUMMARY OF THE INVENTION

The present invention generally relates to systems and methods of optical computing and, more specifically, to systems and methods of determining a particular characteristic of a substance using two or more integrated computational elements.

In some embodiments of the disclosure, a device is disclosed that may include an electromagnetic radiation source configured to optically interact with a sample having a characteristic of interest, and a first integrated computational element arranged within a primary channel and configured to optically interact with the electromagnetic radiation source and produce a first modified electromagnetic radiation. The device may also include a second integrated computational element arranged within a reference channel and configured to optically interact with the electromagnetic radiation source and produce a second modified electromagnetic radiation, and a first detector arranged to receive the first and second modified electromagnetic radiations from the first and second integrated computational elements, respectively, and generate an output signal corresponding to the characteristic of the sample.

In some embodiments of the disclosure, a method of determining a characteristic of a sample is disclosed. The method may include optically interacting an electromagnetic radiation source with the sample and a first integrated computational element arranged within a primary channel and a second integrated computational element arranged within a reference channel. The method may also include producing first and second modified electromagnetic radiations from the first and second integrated computational elements, respectively, and receiving the first and second modified electromagnetic radiations with a first detector. The method may further include generating an output signal with the first detector, the output signal corresponding to the characteristic of the sample.

In some embodiments of the disclosure, another device is disclosed and may include an electromagnetic radiation source configured to optically interact with a sample having a characteristic of interest, and a first integrated computational element arranged within a primary channel and configured to optically interact with the electromagnetic radiation source and produce a first modified electromagnetic radiation. The device may also include a second integrated computational element arranged within a second channel and configured to optically interact with the electromagnetic radiation source and produce a second modified electromagnetic radiation, and a first detector arranged to receive the first modified electromagnetic radiation and generate a first output signal. The device may further include a second detector arranged to receive the second modified electromagnetic radiation and generate a second output signal, and a signal processor configured to receive and computationally combine the first and second output signals to determine the characteristic of interest of the sample.

In some embodiments of the disclosure, another method of determining a characteristic of a sample is disclosed. The method may include optically interacting an electromagnetic radiation source with the sample and a first integrated computational element arranged within a primary channel and a second integrated computational element arranged within a reference channel, and producing first and second modified electromagnetic radiations from the first and second integrated computational elements, respectively. The method may also include receiving the first modified electromagnetic radiation with a first detector, and receiving the second modified electromagnetic radiation with a second detector. The method may further include generating a first output signal with the first detector and a second output signal with the second detector, and computationally combining the first and second output with a signal processor to determine the characteristic of interest of the sample.

The features and advantages of the present invention will be readily apparent to one having ordinary skill in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modification, alteration, and equivalents in form and function, as will occur to one having ordinary skill in the art and having the benefit of this disclosure.

DETAILED DESCRIPTION

Figure 1:
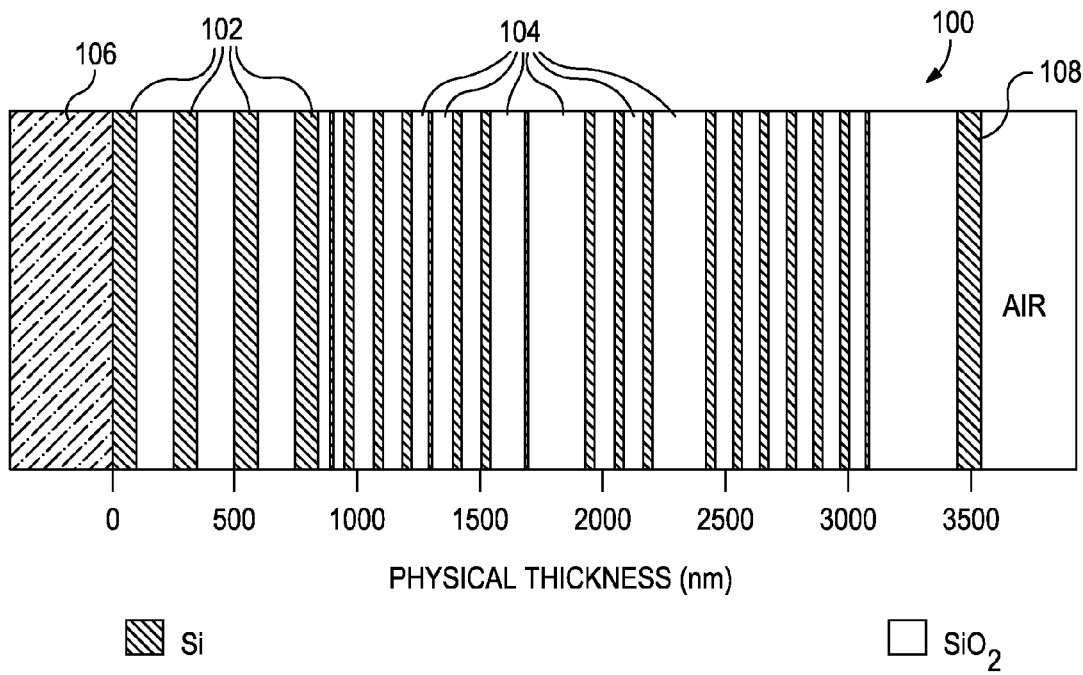
FIG. 1 illustrates an exemplary integrated computation element, according to one or more embodiments.

The present invention generally relates to systems and methods of optical computing and, more specifically, to systems and methods of determining a particular characteristic of a substance using two or more integrated computational elements.

Embodiments described herein include various configurations of optical computing devices, also commonly referred to as opticoanalytical devices. The various embodiments of the disclosed optical computing devices may be suitable for use in the oil and gas industry. For example, embodiments disclosed herein provide systems and/or devices capable of providing a relatively low cost, rugged, and accurate system for monitoring petroleum quality for the purpose of optimizing decision making at a well site and efficient management of hydrocarbon production. Embodiments disclosed herein may also be useful in determining concentrations of various analytes of interest in hydrocarbons present within a wellbore. Embodiments disclosed herein may also be useful in determining concentrations of various analytes of interest in other fluids, such as water, important in the oil and gas industry. It will be appreciated, however, that the various disclosed systems and devices are equally applicable to other technology fields including, but not limited to, the food and drug industry, industrial applications, mining industries, or any field where it may be advantageous to determine in real-time the concentrations of a specific character or analyte of interest of a compound or material.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid. Fluids can include various flowable mixtures of solids, liquid and/or gases. Illustrative gases that can be considered fluids according to the present embodiments include, for example, air, nitrogen, carbon dioxide, argon, helium, hydrogen disulfide, mercaptan, thiophene, methane, ethane, butane, and other hydrocarbon gases, and/or the like.

As used herein, the term "characteristic" refers to a chemical, mechanical, or physical property of a substance. A characteristic of a substance may include a quantitative value of one or more chemical components therein. Such chemical components may be referred to as "analytes." Illustrative characteristics of a substance that can be monitored with the optical computing devices disclosed herein can include, for example, chemical composition (identity and concentration, in total or of individual components), impurity content, pH, viscosity, density, ionic strength, total dissolved solids, salt content, porosity, opacity, bacteria content, combinations thereof, and the like.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation from a substance or sample of the substance and produce an output of electromagnetic radiation from a processing element. The processing element may be, for example, an integrated computational element. The electromagnetic radiation emanating from the processing element is changed in some way so as to be readable by a detector, such that an output of the detector can be correlated to at least one characteristic of the substance. The output of electromagnetic radiation from the processing element can be reflected electromagnetic radiation, transmitted electromagnetic radiation, and/or dispersed electromagnetic radiation. As will be appreciated by those skilled in the art, whether reflected or transmitted electromagnetic radiation is analyzed by the detector will be a matter of routine experimental design. In addition, emission and/or scattering of the substance, for example via fluorescence, luminescence, radiation and re-radiation, Raman scattering, and/or Raleigh scattering can also be monitored by the optical computing devices.

As used herein, the term "optically interact" or variations thereof refers to the reflection, transmission, scattering, diffraction, radiating, re-radiating, or absorption of electromagnetic radiation either on, through, or from one or more processing elements, such as integrated computational elements. Accordingly, optically interacted light refers to light that has been reflected, transmitted, scattered, diffracted, or absorbed by, emitted, radiated, or re-radiated, for example, using the integrated computational elements, but may also apply to interaction with a sample substance.

As used herein, the term "sample," or variations thereof, refers to at least a portion of a substance of interest to be tested or otherwise evaluated using the optical computing devices described herein. The sample includes the characteristic of interest, as defined above, and may be any fluid, as defined herein, or otherwise any solid substance or material such as, but not limited to, rock formations, concrete, other solid surfaces, etc.

At the very least, the exemplary optical computing devices disclosed herein will each include an electromagnetic radiation source, at least two processing elements (e.g., integrated computational elements), and at least one detector arranged to receive optically interacted light from the at least two processing elements. As disclosed below, however, in one or more embodiments, the electromagnetic radiation source may be omitted and instead the electromagnetic radiation may be derived from the substance itself or a sample of the substance. In some embodiments, the exemplary optical computing devices may be specifically configured for detecting, analyzing, and quantitatively measuring a particular characteristic or analyte of interest of a given sample or substance. In other embodiments, the exemplary optical computing devices may be general purpose optical devices, with post-acquisition processing (e.g., through computer means) being used to specifically detect the characteristic of the sample.

In some embodiments, suitable structural components for the exemplary optical computing devices disclosed herein are described in commonly owned U.S. Pat. Nos. 6,198,531; 6,529,276; 7,123,844; 7,834,999; 7,711,605, 7,920,258, and 8,049,881, each of which is incorporated herein by reference in its entirety, and U.S. patent application Ser. No. 12/094,460 (U.S. Pat. App. Pub. No. 2009/0219538); and Ser. No. 12/094,465 (U.S. Pat. App. Pub. No. 2009/0219539), each of which is also incorporated herein by reference in its entirety. As will be appreciated, variations of the structural components of the optical computing devices described in the above-referenced patents and patent applications may be suitable, without departing from the scope of the disclosure, and therefore should not be considered limiting to the various embodiments disclosed herein.

The optical computing devices described in the foregoing patents and patent applications combine the advantage of the power, precision and accuracy associated with laboratory spectrometers, while being extremely rugged and suitable for field use. Furthermore, the optical computing devices can perform calculations (analyses) in real-time or near real-time without the need for sample processing. In this regard, the optical computing devices can be specifically configured to detect and analyze particular characteristics and/or analytes of interest. As a result, interfering signals are discriminated from those of interest in a sample by appropriate configuration of the optical computing devices, such that the optical computing devices provide a rapid response regarding the characteristics of the sample as based on the detected output. In some embodiments, the detected output can be converted into a voltage that is distinctive of the magnitude of the characteristic being monitored in the sample. The foregoing advantages and others make the optical computing devices, and their variations generally described below, particularly well suited for field and downhole use.

The exemplary optical computing devices described herein can be configured to detect not only the composition and concentrations of a material or mixture of materials, but they also can be configured to determine physical properties and other characteristics of the material as well, based on their analysis of the electromagnetic radiation received from the sample. For example, the optical computing devices can be configured to determine the concentration of an analyte and correlate the determined concentration to a characteristic of a substance by using suitable processing means. As will be appreciated, the optical computing devices may be configured to detect as many characteristics or analytes as desired in a given sample. All that is required to accomplish the monitoring of multiple characteristics or analytes is the incorporation of suitable processing and detection means within the optical computing device for each characteristic or analyte. In some embodiments, the properties of a substance can be a combination of the properties of the analytes therein (e.g., a linear, non-linear, logarithmic, and/or exponential combination). Accordingly, the more characteristics and analytes that are detected and analyzed using the exemplary optical computing devices, the more accurately the properties of the given sample can be determined.

Fundamentally, optical computing devices utilize electromagnetic radiation to perform calculations, as opposed to the hardwired circuits of conventional electronic processors. When electromagnetic radiation interacts with a substance, unique physical and chemical information about the substance is encoded in the electromagnetic radiation that is reflected from, transmitted through, or radiated from the sample. This information is often referred to as the substance's spectral "fingerprint." The exemplary optical computing devices disclosed herein are capable of extracting the information of the spectral fingerprint of multiple characteristics or analytes within a substance and converting that information into a detectable output regarding the overall properties of a sample. That is, through suitable configurations of the exemplary optical computing devices, electromagnetic radiation associated with characteristics or analytes of interest in a substance can be distinguished from electromagnetic radiation associated with all other components of a sample in order to estimate the sample's properties in real-time or near real-time.

The processing elements used in the exemplary optical computing devices described herein may be characterized as integrated computational elements (ICE). The ICE are capable of distinguishing electromagnetic radiation related to the characteristic or analyte of interest from electromagnetic radiation related to other components of a sample substance. Referring to FIG. 1, illustrated is an exemplary ICE 100 suitable for use in the various optical computing devices described herein, according to one or more embodiments. As illustrated, the ICE 100 may include a plurality of alternating layers 102 and 104, such as silicon (Si) and $SiO_2$ (quartz), respectively. In general, these layers consist of materials whose index of refraction is high and low, respectively. Other examples might include niobia and niobium, germanium and germania, MgF, SiO, and other high and low index materials as known in the art. The layers 102, 104 may be strategically deposited on an optical substrate 106. In some embodiments, the optical substrate 106 is BK-7 optical glass. In other embodiments, the optical substrate 106 may be other types of optical substrates, such as quartz, sapphire, silicon, germanium, zinc selenide, zinc sulfide, or various plastics such as polycarbonate, polymethalmethacrylate (PMMA), polyvinylchloride (PVC), diamond, ceramics, etc., as known in the art.

At the opposite end (e.g., opposite the optical substrate 106), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of the sample substance using a conventional spectroscopic instrument. The spectrum of interest of a given characteristic of a sample typically includes any number of different wavelengths. It should be understood that the exemplary ICE 100 in FIG. 1 does not in fact represent any particular characteristic of a given sample, but is provided for purposes of illustration only. Consequently, the number of layers 102, 104 and their relative thicknesses, as shown in FIG. 1, bear no correlation to any particular characteristic of a given sample. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the material to the sample substance. For example, the layers 102, 104 may be made of, but are not limited to, silicon, germanium, water, combinations thereof, or other materials of interest.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown) which houses the gases or liquids. Exemplary variations of the ICE 100 may also include holographic optical elements, gratings, piezoelectric, light pipe, digital light pipe (DLP), and/or acousto-optic elements, for example, that can create transmission, reflection, and/or absorptive properties of interest.

The multiple layers 102, 104 exhibit different refractive indices. By properly selecting the materials of the layers 102, 104 and their relative spacing, the exemplary ICE 100 may be configured to selectively pass/reflect/refract predetermined fractions of light (i.e., electromagnetic radiation) at different wavelengths. Each wavelength is given a predetermined weighting or loading factor. The thicknesses and spacing of the layers 102, 104 may be determined using a variety of approximation methods from the spectrograph of the character or analyte of interest. These methods may include inverse Fourier transform (IFT) of the optical transmission spectrum and structuring the ICE 100 as the physical representation of the IFT. The approximations convert the IFT into a structure based on known materials with constant refractive indices. Further information regarding the structures and design of exemplary integrated computational elements (also referred to as multivariate optical elements) is provided in *Applied Optics*, Vol. 35, pp. 5484-5492 (1996) and Vol. 129, pp. 2876-2893, which is incorporated by reference herein to the extent not inconsistent with the present disclosure.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest. Further details regarding how the exemplary ICE 100 is able to distinguish and process electromagnetic radiation related to the characteristic or analyte of interest are described in U.S. Pat. Nos. 6,198,531; 6,529,276; and 7,920,258, previously incorporated herein by reference.

Figure 2A:
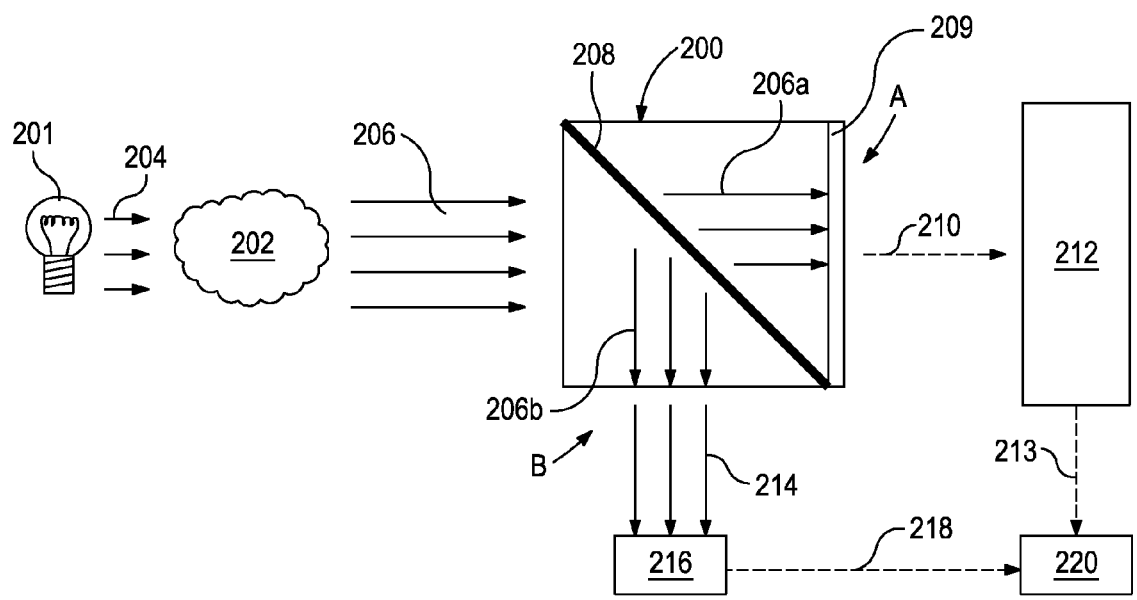
FIG. 2a illustrates a block diagram non-mechanistically illustrating how an optical computing device distinguishes electromagnetic radiation related to a characteristic of interest from other electromagnetic radiation, according to one or more embodiments.

Referring now to FIG. 2a, illustrated is a block diagram that non-mechanistically illustrates how an optical computing device 200 is able to distinguish electromagnetic radiation related to a characteristic of a sample 202 from other electromagnetic radiation. As shown in FIG. 2a, an electromagnetic radiation source 201 emits or otherwise generates electromagnetic radiation 204. The electromagnetic radiation source 201 may be any device capable of emitting or generating electromagnetic radiation, as defined herein. In some embodiments, the electromagnetic radiation source 201 is a light bulb, light emitting device (LED), laser, blackbody, photonic crystal, or X-Ray source, or the like. The electromagnetic radiation 204 is directed toward the sample 202, which contains an analyte of interest (e.g., a characteristic of the sample) desired to be determined. The electromagnetic radiation 204 optically interacts with the sample 202 and produces optically interacted radiation 206 (e.g., sample-interacted light), some of which may be electromagnetic radiation corresponding to the characteristic or analyte of interest and some of which may be background electromagnetic radiation corresponding to other components or characteristics of the sample 202.

While FIG. 2a shows the electromagnetic radiation 204 as passing through the sample 202 to produce the optically interacted radiation 206, it is also contemplated herein to reflect the electromagnetic radiation 204 off of the sample 202, such as may be required when the sample 202 is translucent, opaque, or solid. Accordingly, reflecting the electromagnetic radiation 204 off of the sample 202 also generates the optically interacted radiation 206. Moreover, in some embodiments, the electromagnetic radiation source 201 may be omitted altogether and the required electromagnetic radiation may be derived from the sample 202 itself. For example, various substances naturally radiate electromagnetic radiation. For instance, the sample 202 may be a blackbody radiating substance configured to radiate electromagnetic radiation in the form of heat. In other embodiments, the sample 202 may be radioactive or chemo-luminescent and therefore radiate electromagnetic radiation. In yet other embodiments, the required electromagnetic radiation may be induced from the sample 202 by being acted upon mechanically, magnetically, electrically, combinations thereof, or the like.

Although not specifically shown, one or more spectral elements may be employed in the device 200 in order to restrict the optical wavelengths and/or bandwidths of the system and thereby eliminate unwanted electromagnetic radiation existing in wavelength regions that have no importance. Such spectral elements can be located anywhere along the optical train, but are typically employed directly after the electromagnetic radiation source 201. Various configurations and applications of spectral elements in optical computing devices may be found in commonly owned U.S. Pat. Nos. 6,198,531; 6,529,276; 7,123,844; 7,834,999; 7,711,605, 7,920,258, 8,049,881, and U.S. patent application Ser. No. 12/094,460 (U.S. Pat. App. Pub. No. 2009/0219538); Ser. No. 12/094,465 (U.S. Pat. App. Pub. No. 2009/0219539), incorporated herein by reference, as indicated above.

The optically interacted radiation 206 may impinge upon the optical computing device 200, which may contain, for example, a beam splitter 208. The beam splitter 208 may be configured to split the optically interacted radiation 206 into a first beam of light 206a directed in a first channel A and a second beam of light 206b directed in a second channel B. As used herein, the term "channel" refers generally to an optical path or optical train, as known in the art. The first channel A is configured to direct the first beam of light 206a toward an ICE 209, thus the first channel A may be characterized as or otherwise called a "primary" channel. The ICE 209 may be substantially similar to the ICE 100 described above with reference to FIG. 1. The ICE 209 may be configured to produce modified electromagnetic radiation 210 corresponding to the characteristic or analyte of interest. In particular, the modified electromagnetic radiation 210 may include electromagnetic radiation that has optically interacted with the ICE 209, whereby approximate mimicking of the regression vector corresponding to the characteristic of interest is obtained.

Within the primary channel A, the modified electromagnetic radiation 210 is subsequently conveyed to a detector 212 for quantification. The detector 212 may be any device capable of detecting electromagnetic radiation, and may be generally characterized as an optical transducer. For example, the detector 212 may be, but is not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, and/or combinations thereof, or the like, or other detectors known to those skilled in the art.

In some embodiments, the detector 212 is configured to produce an output signal 213 in the form of a voltage (or current) that corresponds to the particular characteristic of the sample 202. In at least one embodiment, the output signal 213 produced by the detector 212 and the concentration of the characteristic of the sample 202 may be directly proportional. In other embodiments, however, the relationship may correspond to a polynomial function, an exponential function, and/or a logarithmic function, or a combination thereof.

The second beam of light 206b may be directed within the second channel B toward a second detector 216. The second detector 216 may be similar to the first detector 212, such as by being any device capable of detecting electromagnetic radiation. Without limitation, the second detector 216 may be used to detect radiating deviations stemming from the electromagnetic radiation source 201. Undesirable radiating deviations can occur in the intensity of the light in the primary channel A due to a wide variety of reasons and causing various negative effects. These negative effects can be particularly detrimental for measurements taken over a period of time. Radiating deviations can include such things as, but not limited to, light intensity fluctuations of the electromagnetic radiation 204. It can also include interferent fluctuations, which may scatter or absorb light from the sample 202 as it moves through the interaction space as might occur if a foreign substance such as dirt or dust is entrained within the sample 202 or otherwise passes in front of the electromagnetic radiation source 201. Radiating deviations can also include a film of material build-up on the windows of the interrogation space which has the effect of reducing the amount of light reaching the detector 216. Without proper compensation, such radiating deviations could result in false readings from the primary channel A, and the output signal 213 would no longer be primarily related to the characteristic of interest.

To correct or compensate for these types of undesirable effects, the second detector 216 arranged in the second channel B may be configured to generate a compensating signal 218 generally indicative of the radiating deviations of the electromagnetic radiation source 201, and thereby normalize the output signal 213. Accordingly, the second channel B is typically characterized as or otherwise referred to in the art as a "reference" channel. In some applications, the compensating signal 218 and the output signal 213 may be transmitted to or otherwise received by a signal processor 220 communicably coupled to both the detectors 212, 216. The signal processor 220 may be a computer including a non-transitory machine-readable medium, as discussed in more detail below. The signal processor 220 may be configured to computationally combine the compensating signal 218 with the output signal 213 in order to normalize the output signal 213 in view of any radiating deviations as detected by the second detector 216. In some embodiments, computationally combining the output and compensating signals 213, 218 may entail computing a ratio of the two signals 213, 218, thereby essentially computing a ratio of the primary and reference channels A and B (e.g., A/B).

It should be noted that the reference channel B is created in a manner which does not detrimentally change the predictive characteristics of ICE 209 arranged in the primary channel A. For example, if the beamsplitter 208 were replaced with a spectral element (e.g., one whose transmittance or reflectance has a variation with wavelength), then the spectral characteristics of the light incident upon the ICE 209 arranged in the primary channel A would be altered, and the light emerging from the ICE 209 would have its spectral characteristics and intensity changed from the original design, with a generally negative consequence. Viewed another way, a spectrally active element would modify the intended transmission (or reflection) spectrum of the ICE 209 which was originally and carefully designed to mimic the regression vector associated with the analyte or characteristic of interest. Thus, reference channel B is generally created by detecting a portion of the light beam before striking the ICE 209. Spectrally neutral elements (e.g., elements whose transmittance, absorbance, and/or reflectance do not vary substantially with wavelength) are generally used to create the reference channel B. At least some spectrally neutral elements that may be used are, but are not limited to, neutral density filters and beamsplitters, partially transparent masks, front surface Fresnel reflections, combinations thereof, or similar components.

The signal processor 220 may also be configured to further process the output and compensating signals 213, 218 in order to provide additional characterization information about the sample 202 being analyzed. In some embodiments, the identification and concentration of each analyte in the sample 202 can be used to predict certain physical characteristics of the sample 202. For example, the bulk characteristics of a sample 202 can be estimated by using a combination of the properties conferred to the sample 202 by each analyte.

In some embodiments, the concentration of each analyte or the magnitude of each characteristic determined using the optical computing device 200 can be fed into an algorithm run by the signal processor 220. The algorithm may be configured to make predictions on how the characteristics of the sample 202 change if the concentrations of the analytes are changed relative to one another. In some embodiments, the algorithm produces an output that is readable by an operator who can consider the results and make proper adjustments or take appropriate action, if needed, based upon the output.

The algorithm can be part of an artificial neural network configured to use the concentration of each detected analyte in order to evaluate the characteristic(s) of the sample 202 and, if desired, predict how to modify the sample 202 in order to alter its properties in a desired way. Illustrative but non-limiting artificial neural networks are described in commonly owned U.S. patent application Ser. No. 11/986,763 (U.S. Patent App. Pub. No. 2009/0182693), which is incorporated herein by reference to the extent not inconsistent with the present disclosure. It is to be recognized that an artificial neural network can be trained using samples having known concentrations, compositions, and/or properties, thereby generating a virtual library. As the virtual library available to the artificial neural network becomes larger, the neural network can become more capable of accurately predicting the characteristics of a sample having any number of analytes present therein. Furthermore, with sufficient training, the artificial neural network can more accurately predict the characteristics of the sample, even in the presence of unknown analytes.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory [e.g., random access memory (RAM), flash memory, read only memory (ROM), programmable read only memory (PROM), erasable read only memory (EPROM)], registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium refers to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site.

Figure 2B:
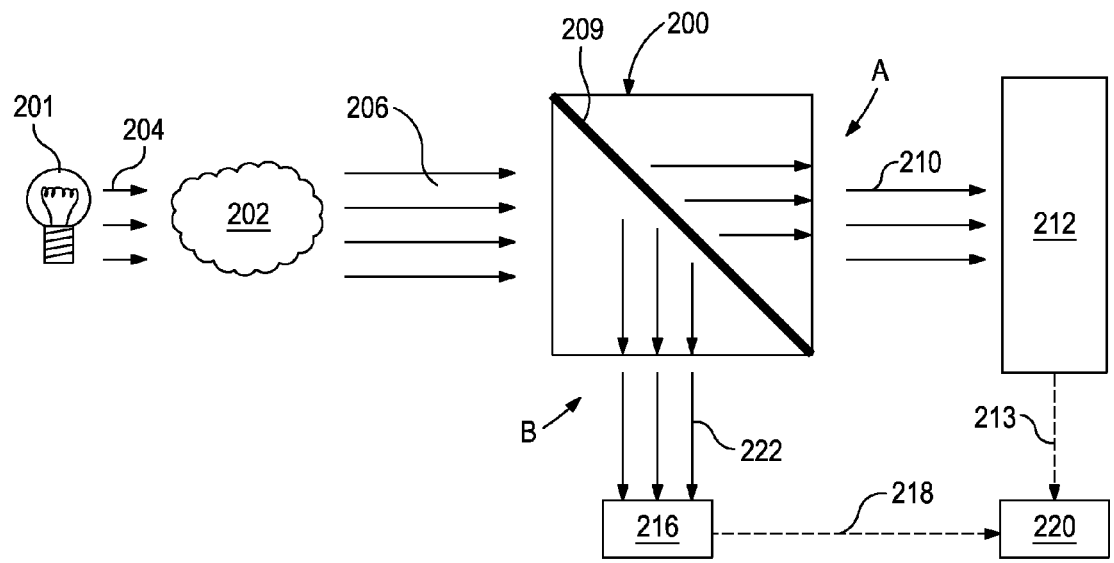
FIG. 2b illustrates another block diagram non-mechanistically illustrating how an optical computing device distinguishes electromagnetic radiation related to a characteristic of interest from other electromagnetic radiation, according to one or more embodiments.

Referring to FIG. 2b, illustrated is an exemplary variation of the optical computing device 200 described above with reference to FIG. 2a. In FIG. 2b, the beam splitter is replaced with the ICE 209 which now essentially functions like a beam splitter. Specifically, the optically interacted radiation 206 may impinge upon the ICE 209 which may be configured to transmit a first modified electromagnetic radiation 210 in the primary channel A and reflect a second modified electromagnetic radiation 222 in the reference channel B. Each of the first and second modified electromagnetic radiations 210, 222 may correspond to the characteristic or analyte of interest. In particular, the modified electromagnetic radiations 210, 222 may each include electromagnetic radiation that has optically interacted with the ICE 209, whereby approximation mimicking of the regression vector corresponding to the characteristic of interest is obtained. In use, however, the signal from the reference channel B may be used to normalize the signal from the primary channel A, as generally described above.

For instance, the first detector 212 receives the first modified electromagnetic radiation 210 and provides the output signal 213 to the signal processor 220, and the second detector 216 receives the second modified electromagnetic radiation 222 and provides the compensating signal 218 to the signal processor. The signal processor 220 computationally combines the compensating signal 218 with the output signal 213 in order to normalize the output signal 213 in view of any radiating deviations as detected by the second detector 216. In the illustrated embodiment, where the second modified electromagnetic radiation 222 also provides an approximate mimicking of the regression vector corresponding to the characteristic of interest, computationally combining the output and compensating signals 213, 218 may entail computing a ratio of the output signal 210 and the sum of the output signal 210 and the compensating signal 218. In other words, the signal processor 220 may be configured to compute the ratio of the signal derived from the primary channel A and the sum of the signals derived from both the primary and compensating channels A,B (i.e., A/(A+B)).

Figure 3A:
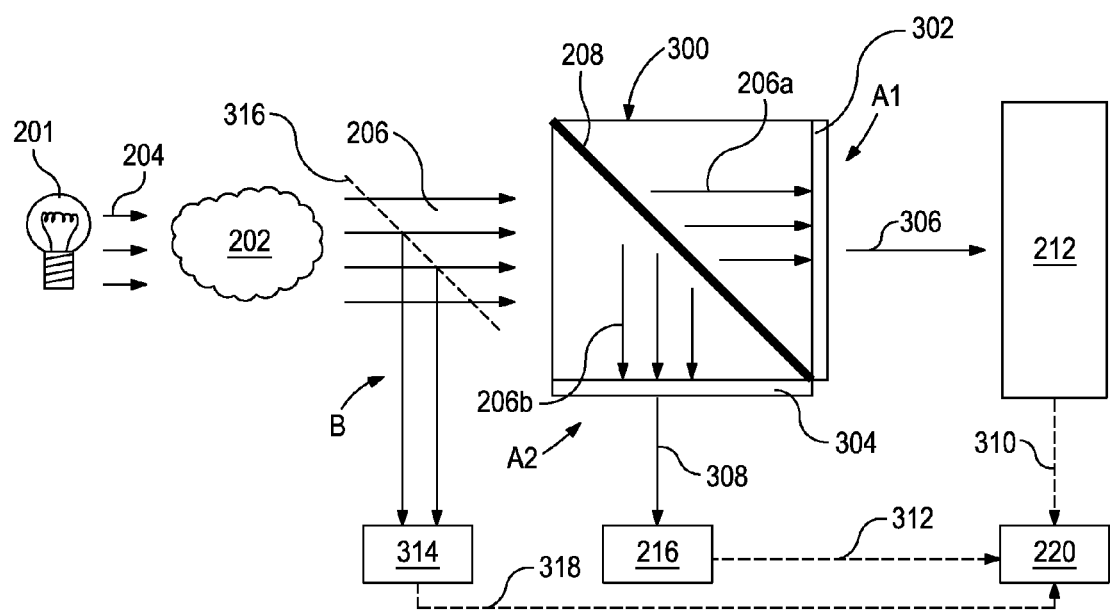
FIG. 3a illustrates an exemplary optical computing device, according to one or more embodiments.

Referring now to FIG. 3a, illustrated is another optical computing device 300 also configured to determine a characteristic of interest of the sample 202. The optical computing device 300 may be similar in several respects to the optical computing device 200 described above with reference to FIGS. 2a and 2b. Accordingly, the device 300 may be best understood with reference to FIGS. 2a and 2b, where like numerals represent like elements that will not be described again in detail. Similar to the device 200 discussed above, the optical computing device 300 receives an output of optically interacted radiation 206 emitted from the sample 202 after the sample 202 has been illuminated with electromagnetic radiation 204 from the electromagnetic radiation source 201. Unlike the optical computing device 200, however, the optical computing device 300 may include at least two ICEs, illustrated as a first ICE 302 and a second ICE 304. The first and second ICE 302, 304 may be generally similar in construction to the ICE 100 described above with reference to FIG. 1, but may also vary from each other depending on the application, as will be better understood from the discussion below.

In some embodiments, the first and second ICE 302, 304 may be configured to be associated with a particular characteristic of the sample 202. In other words, the first and second ICE 302, 304 may be especially designed in their respective layers, thicknesses, and materials so as to correspond with the spectral attributes associated with the characteristic of interest. Each of the first and second ICE 302, 304, however, may be designed entirely different from each other, thereby approximating or otherwise mimicking the regression vector of the characteristic in entirely different ways. In other embodiments, however, one or both of the first and second ICE 302, 304 may be entirely or substantially disassociated with the characteristic of interest. Briefly, manufacturing an ICE can be a very complex and intricate process. In addition, when an ICE is manufactured specifically to mimic the regression vector of a characteristic of interest, this process can become even more complicated. As a result, it is common to produce non-predictive, or poorly made ICE that, when tested, fail to accurately or even remotely be associated with the characteristic of interest (e.g., a disassociated ICE). In some cases, these non-predictive ICE may return an arbitrary regression vector when tested or otherwise exhibit an arbitrary transmission function. In other cases, the non-predictive ICE may be considered "substantially" disassociated with the characteristic of interest in that the ICE only slightly mimics the regression vector of the characteristic but is nonetheless considered non-predictive. In yet other cases, the non-predictive ICE may return a regression vector that closely mimics another characteristic of the substance being tested, but not the characteristic of interest.

Additional information and advantages of using multiple associated or disassociated ICE in optical computing devices to determine a single characteristic of interest is further described in co-pending U.S. patent application Ser. Nos. 13/456,264 and 13/456,283, filed herewith concurrently, the contents of which are hereby incorporated by reference in their entireties.

As shown in FIG. 3a, the optically interacted radiation 206 is directed to the optical computing device 300 and the beam splitter 208 again separates the optically interacted radiation 206 into first and second beams of light 206a,b. The first beam of light 206a is directed into the first or primary channel A1 and conveyed to the first ICE 302 which generates a first modified electromagnetic radiation 306 corresponding to the characteristic or analyte of interest of the sample 202. The first detector 212 may be arranged to receive the first modified electromagnetic radiation 306 from the first ICE 302 and quantify the resulting signal in the form of a first output signal 310.

As illustrated, the second ICE 304 is arranged within what would normally be used as a reference channel configured to normalize the first output signal 310 derived from the primary channel A1 in view of radiating deviations of the electromagnetic radiation source 201. Arranging the second ICE 304 in the typical reference channel, however, now provides a new type of reference channel A2 and, similar to the primary channel A1, the reference channel A2 is also configured to provide an output corresponding to the characteristic or analyte of interest of the sample 202. Consequently, the reference channel A2 may also be considered, in at least some cases, as a primary channel of the device 300, substantially similar to the first primary channel A1. As will discussed below, embodiments are contemplated herein which include several primary "A" channels in a single optical computing device, where each primary "A" channel is configured to provide an output corresponding to the characteristic or analyte of interest of the sample 202.

In FIG. 3a, the second beam of light 206b is directed into the reference channel A2 and conveyed to the second ICE 304 which generates a second modified electromagnetic radiation 308 corresponding to the characteristic or analyte of interest of the sample 202. The second detector 216 may be arranged to receive the second modified electromagnetic radiation 308 from the second ICE 304 and quantify the resulting signal in the form of a second output signal 312.

As illustrated, the optical computing device 300 may further include a third detector 314, according to one or more embodiments. The third detector 314 may be substantially similar to the first and second detectors 212, 216 and may be used in the device 300 to detect radiating deviations stemming from the electromagnetic radiation source 201. Accordingly, a second or true reference channel B may be included in the device 300 and may serve the same purpose as the reference channel B described above with reference to FIGS. 2a and 2b. As illustrated, a beam splitter 316 may be arranged to reflect a portion of the optically interacted light 206 toward the third detector 314 in order to generate a compensating signal 318 generally indicative of radiating deviations, as generally described above. In other embodiments, however, the third detector 314 may be arranged so as to receive electromagnetic radiation 204 directly from the electromagnetic source 201 or electromagnetic radiation reflected off of either of the ICE 302, 304 and likewise generate the compensating signal 318.

The first and second output signals 310, 312 may then be received by and computationally combined in the signal processor 220 to determine the characteristic of interest in the sample 202. In one or more embodiments, computationally combining the first and second output signals 310, 312 is desired. This computation may involve a variety of mathematical relationships, including, for example, a linear relationship, a polynomial function, an exponential function, and or a logarithmic function, or a combination thereof. In these cases, a variety of normalization mathematics between the output signals 310, 312 and the compensating signal 318 may be applied in order to take into account any radiating deviations detected by the third detector 314. For example, the output signals 310, 312 may each be normalized by dividing each by the compensating signal 318 to achieve, for example, A1/B and A2/B, before the mathematical relationship between A1/B and A2/B is applied. In other cases, the mathematical relationship between A1 and A2 may be applied, with the resultant normalized by channel B. In even other cases, a combination of these two normalization methods may be applied. Those skilled in the art will be familiar with both general methods, and can choose which method is most applicable given the specific relationships involved. Finally, it is understood by those skilled in the art that fractions or multiples of the quantity B may be employed, as well as multiplication of the quantity (1/B).

Figure 3B:
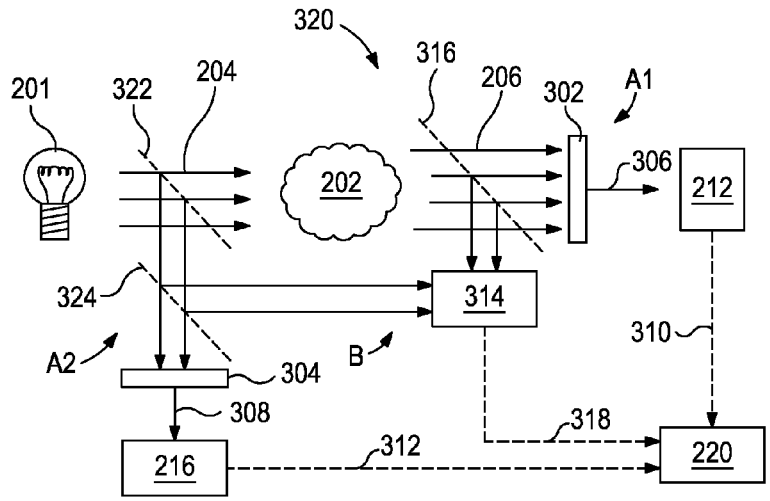
FIG. 3b illustrates another exemplary optical computing device, according to one or more embodiments.

Referring now to FIG. 3b, illustrated is another exemplary optical computing device 320, according to one or more embodiments. The device 320 may be substantially similar to the device 300 described above with reference to FIG. 3a and therefore may be best understood with reference thereto, where like numerals represent like elements not described again in detail. In FIG. 3b, the optically interacted radiation 206 is again directed into the first or primary channel A1 and conveyed to the first ICE 302 which generates a first modified electromagnetic radiation 306 corresponding to the characteristic or analyte of interest of the sample 202. The first detector 212 receives the first modified electromagnetic radiation 306 from the first ICE 302 and provides the first output signal 310.

The second ICE 304 may again be arranged within what could normally be used as a reference channel for the device 320 and otherwise used to normalize the first output signal 310 derived from the primary channel A1 in view of radiating deviations of the electromagnetic radiation source 201. Specifically, the second ICE 304 is arranged in new reference channel A2 and, similar to the primary channel A1, may be configured to provide an output corresponding to the characteristic or analyte of interest of the sample 202. As depicted, the second ICE 304 may be configured to optically interact with a portion of the electromagnetic radiation 204 directly radiated by the electromagnetic radiation source 201. In one or more embodiments, a beam splitter 322 may be configured to split the electromagnetic radiation 204 and direct a portion thereof toward the second ICE 304. In other embodiments, however, the second ICE 304 may be arranged so as to receive the electromagnetic radiation 204 directly from the electromagnetic radiation source 201, instead of receiving a reflected portion thereof. Those skilled in the art will readily recognize that the reference channel A2 may be defined in a variety of locations within the optical computing device 320, or any of those described herein, without departing from the scope of the disclosure.

The second ICE 304 generates the second modified electromagnetic radiation 308 and conveys the same to the second detector 216. The second detector 216 may be configured to receive and quantify the second electromagnetic radiation 308 and provide the second output signal 312 which may be directed toward the signal processor 220.

As illustrated, the optical computing device 320 may further include the third detector 314 used to detect radiating deviations stemming from the electromagnetic radiation source 201. In one embodiment, the third detector 314 may be arranged to receive a portion of the optically interacted light 206 as reflected from the beam splitter 316. In other embodiments, however, the third detector 314 may be arranged to receive a portion of the electromagnetic radiation 204 as reflected from another beam splitter 324 arranged within the reflected portion of the electromagnetic radiation 204 as derived from the first beam splitter 322. Accordingly, a true reference channel B may also be included in the device 300 and may serve the same purpose as the reference channel B described above with reference to FIGS. 2a and 2b. As illustrated, a beam splitter 316 may be arranged to reflect a portion of the optically interacted light 206 toward the third detector 314 in order to generate a compensating signal 318 generally indicative of radiating deviations, as generally described above.

The compensating signal 318 in the second reference channel B may be directed to the signal processor 220 and computationally combined with the first and second output signals 310, 312 derived from the primary and first reference channels A1, A2, respectively, in order to compensate for any electromagnetic radiating deviations stemming from the electromagnetic radiation source 201. As discussed above, the ratio of the light intensity derived from the primary and first reference channels A1, A2 is divided by the light intensity derived from the second reference channel B, and the resulting output is related to the analyte concentration or characteristic of interest. In one embodiment, for example, the compensating signal 318 and the first and second output signals 310, 312 are combined using principal component analysis techniques such as, but not limited to, standard partial least squares which are available in most statistical analysis software packages (e.g., XL Stat for MICROSOFT® EXCEL®; the UNSCRAMBLER® from CAMO Software and MATLAB® from MATHWORKS®). In other embodiments, the compensating signal 318 is used simply to inform the user of the condition of the electromagnetic radiation source 201, e.g., whether the source 201 is functioning properly.

As will be appreciated by those skilled in the art, more than two ICE 302, 304 may be used in alternative configurations or embodiments, without departing from the scope of the disclosure. Moreover, it should be noted that while FIGS. 3a and 3b show electromagnetic radiation as being transmitted through the first and second ICE 302, 304 in order to generate the first and second modified electromagnetic radiations 306, 308, respectively, it is also contemplated herein to reflect the electromagnetic radiation off of the first and second ICE 302, 304 and equally generate the corresponding first and second modified electromagnetic radiations 306, 308, without departing from the scope of the disclosure.

It has been discovered that usage of one or more ICE in both the primary and reference channels A1, A2 may enhance the sensitivity and detection limits of the optical computing device 300 beyond what would otherwise be attainable with a single ICE design that utilizes a dedicated reference channel B for normalizing electromagnetic radiation fluctuations, such as is described above with reference to FIGS. 2a and 2b. This was entirely unexpected and would be considered wholly unobvious to those skilled in the art. For instance, the typical reference channel B in optical computing devices is a spectrally neutral channel and therefore dedicated solely to providing a ratio denominator useful in normalizing the output signal derived from the primary channel A against radiating deviations. Placing an ICE in the reference channel B would be wholly unobvious since the ICE is designed to be spectrally active and therefore has a spectrum associated with it which optically interacts with the second light beam 206b and changes its spectral characteristics. Accordingly, with the second ICE 304 arranged in the reference channel A2, as depicted in FIG. 3a, the reference channel is no longer used for its intended purpose but nonetheless has been found to dramatically increase the sensitivities and detection limits of the device 300. These unexpected results are especially possible even in the presence of various interferents.

As further explanation, methods of how to design and build single ICE elements with optimal performance characteristics are disclosed in U.S. Pat. No. 7,711,605 and U.S. Pat. Pub. No. 2010/0153048, incorporated herein by reference to the extent not inconsistent with the present disclosure. Using the methods described therein, literally thousands and hundreds of thousands of individual unique designs are created and optimized for performance, thereby exhausting the optimal solution space available and yielding the best solutions possible. Those skilled in the art will readily recognize that ICE designs can be particularly sensitive to small changes in their optical characteristics. Thus, any modification of the optical characteristic (e.g., changes made to the particular transmission function) with, for example, additional ICE components, would be considered as degrading the performance of the optical computing device, and in most cases, quite rapidly with only small changes. And indeed, it has been discovered that spectral components (i.e., ICE components or designs) arranged in the reference channel B do degrade the overall performance in some instances.

However, it was unexpectedly discovered that, in at least some case, some spectral components, including some preferred ICE designs, may enhance overall device performance when arranged in the reference channel B. It was further discovered, that these enhancements are not minor adjustments or improvements, but may enhance performance involving factors and/or orders of magnitude of improvement. It was yet further discovered that performance enhancements can be obtained without substantial compromise or trade-off of other important characteristics. It was also discovered that the ICE arranged in the reference channel B may or may not be configured to be associated with the characteristic of the sample.

Figure 4:
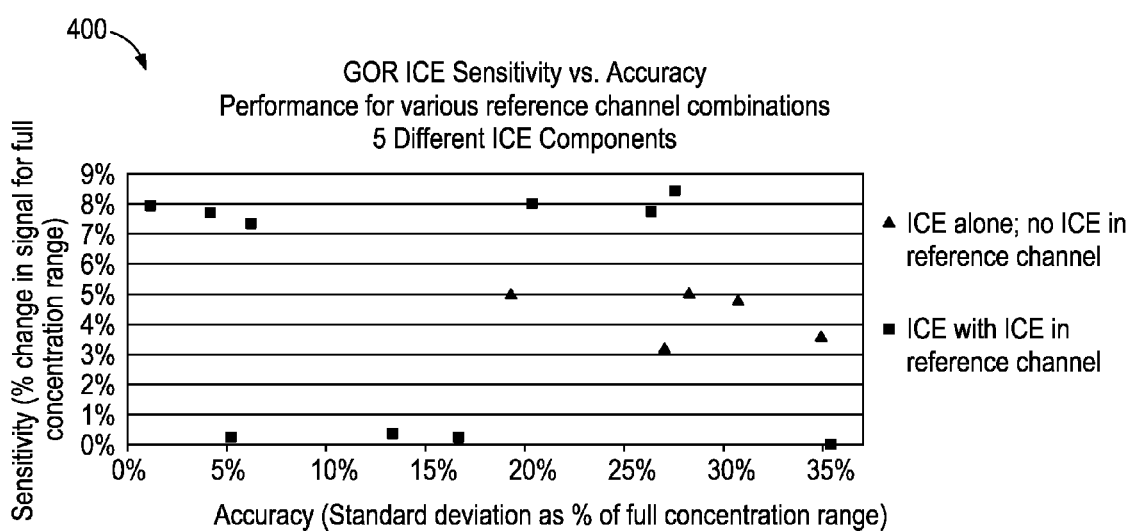
FIG. 4 illustrates a graph indicating the advantages of arranging integrated computational elements in both the primary and reference channels, according to one or more embodiments.

Referring to FIG. 4, illustrated is a graph 400 indicating the detection of a particular characteristic of a sample using one ICE arranged in the primary channel A, and another ICE in the reference channel B. It will be appreciated that the graph 400 and the data presented therein are merely used to facilitate a better understanding of the present disclosure, and in no way should the they be read to limit or define the scope of the invention. The graph 400 indicates the detection of the methane gas to oil ratio (GOR) in two radically different oils from concentrations from 0 to 1000 scuft/bbl (standard cubic feet per standard barrel) under various pressures and temperatures associated with downhole oil field conditions. The two oils are a black, high asphaltene content optically opaque oil sample obtained from the Gulf of Mexico, and a light, low asphaltene, relatively transparent, high sulfur content oil sample obtained from Saudi Arabia. The graph 400 depicts the accuracy (standard deviation) of measuring the GOR for both oils across the entire 0 to 1000 scuft/bbl concentration range of interest for an optical computing device (e.g., the optical device 300, or any of the exemplary optical computing devices disclosed herein) on the X-axis.

Results are shown for five different individual ICE designs and with the various unique combinations of the five with one of the ICE designs in the reference channel B. As shown, a single ICE design without an ICE in the reference channel B (i.e., shown as triangles) may yield an accuracy ranging between a predictive 19.2% of full scale (190 scuft/bbl) and a non-predictive 34.9% of full scale (349 scuft/bbl).

The sensitivity of the device (e.g., the optical device 300, or any of the exemplary optical computing devices disclosed herein), another key performance attribute important to the detection limits, is also shown in the graph on the Y axis. The units of sensitivity are the absolute magnitude of the % change in detector signal output observed over the entire GOR concentration range (0 to 1000 scuft/bbl) of interest. Regarding sensitivity, the larger the magnitude of the % change, the more sensitive and desirable is the system as greater sensitivity can enable better detectability and performance limits, lower costs, and other important benefits. As shown, sensitivities for the standard configuration involving a neutral reference channel B, but without an ICE arranged in the reference channel B (i.e., shown as triangles), range from 3.3% to 4.9%.

When an ICE design is arranged in the reference channel B, however, the performance may be enhanced (i.e., shown as squares). For example, by placing an ICE in the reference channel B, accuracies may be improved from a non-predictive 34.9% (349 scuft/bbl) to a highly predictive 1.1% (11 scuft/bbl), or about a factor of 17× improvement over the best single ICE with neutral reference case, and about a factor of 31× over the non-predictive case. Sensitivities were also improved for many combinations, obtaining a factor of between 1.5 to almost 3× of that of a single ICE design without a spectral element (i.e., additional ICE) in the reference channel.

Those skilled in the art will readily recognize that increases in sensitivity are often accompanied by corresponding decreases in accuracy for single ICE solutions. Thus, one single ICE design may have superior sensitivity over another, but will generally be found to be less accurate. Accuracy and sensitivity, two of the most important performance parameters for optical computing devices, are therefore generally trade-offs. The improvement in accuracy discovered by using an ICE in the reference channel B, as shown in FIG. 4, was totally unexpected. Even more unexpected was that both the accuracy and sensitivity could be simultaneously increased or at least maintained. For example, three of the unique combinations with an ICE in the reference channel B show both a dramatic enhancement in accuracy and an improvement of approximately 1.5 to 3× in sensitivity. Three showed a substantial improvement in sensitivity (and therefore lower detection limits) while maintaining about the same accuracy.

It should be noted that these unexpected results were not achieved for all combinations of ICE designs in the reference channel B. Instead, there were three combinations, in particular, where the accuracy improved but the sensitivity decreased. Moreover, one combination was tested where the accuracy was not improved, but the sensitivity decreased. However, the graph 400 clearly shows that optical computing device performance can increase by placing a spectral component (e.g., an ICE design) in the reference channel B as opposed to using the traditional non-spectral component. Moreover, the ICE arranged in the reference channel B could either be associated (predictive) or substantially disassociated (non-predictive) with the characteristic of interest (GOR in this case).

Figure 5:
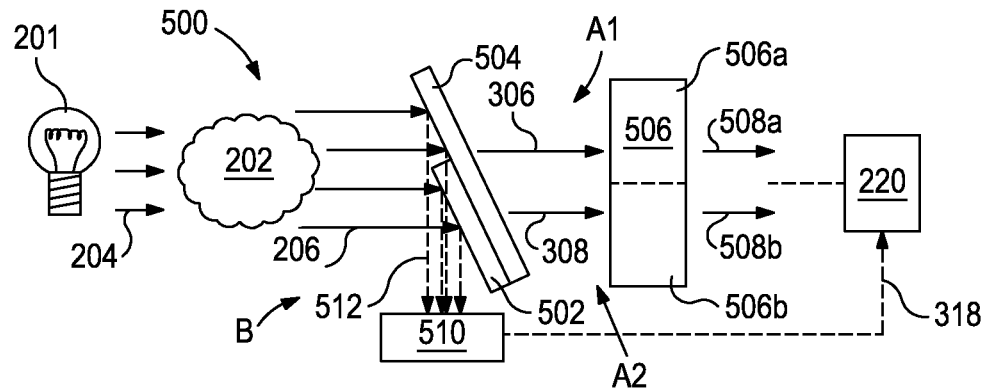
FIG. 5 illustrates another exemplary optical computing device, according to one or more embodiments.

Referring now to FIG. 5, illustrated is another exemplary optical computing device 500, according to one or more embodiments. The device 500 may be somewhat similar to the optical computing device 300 described above with reference to FIG. 3a, and therefore may be best understood with reference to FIG. 3a where like numerals indicate like elements that will not be described again in detail. As illustrated, the device 500 may include a first ICE 502 and a second ICE 504. The first and second ICE 502, 504 may be similar in construction to the ICE 100 described above with reference to FIG. 1, and configured to be either associated or disassociated with a particular characteristic of the sample. Embodiments are contemplated herein that include one or more beam splitters, mirrors, and the like in order to allow the electromagnetic radiation 204 to optically interact with both the sample 202 and first and second ICE 502, 504, without departing from the scope of the disclosure. Indeed, one or more beam splitters, mirrors, and the like may be used in conjunction with any of the exemplary embodiments disclosed herein, without departing from the scope of the disclosure.

As illustrated, the first and second ICE 502, 504 may be coupled together to form a monolithic structure, but in other embodiments may be separated or otherwise arranged in series without departing from the scope of the disclosure. Moreover, the first and second ICE 502, 504 may be arranged to receive the optically interacted light 206, as depicted, but may equally be arranged antecedent to the sample 202 and therefore directly receive the electromagnetic radiation 204. In one embodiment, the first ICE 502 may be smaller than the second ICE 504 or otherwise arranged such that a portion of the optically interacted light 206 passes through only the second ICE 504 and generates the first modified electromagnetic radiation 306. Another portion of the optically interacted light 206 may pass through a combination of both the first and second ICE 502, 504 and thereby generate the second modified electromagnetic radiation 308. As a result, the device 500 may provide a first or primary channel A1 that incorporates the optically interacted light 206 passing through the second ICE 504 and thereafter generating the first modified electromagnetic radiation 306, and a second or reference channel A2 that incorporates the optically interacted light 206 passing through both the first and second ICE 502, 504 and thereafter generating the second modified electromagnetic radiation 308.

The first and second modified electromagnetic radiations 306, 308 may be directed to a detector 506, which may be a split or differential detector, having a first detector portion 506a and a second detector portion 506b. In other embodiments, however, the detector 506 may be a detector array, as known in the art, without departing from the scope of the disclosure. In operation, the first detector portion 506a forms part of the primary channel A1 and may be configured to receive the first modified electromagnetic radiation 306 and generate a first output signal 508a. Furthermore, the second detector portion 506b forms part of the reference channel A2 and may be configured to receive the second modified electromagnetic radiation 308 and generate a second output signal 508b. In some embodiments, the detector 506 may be configured to computationally combine the first and second signals 508a,b in order to determine the characteristic of the sample, for example when using a differential detector or quad-detector. In other embodiments, the first and second signals 508a,b may be transmitted to or otherwise received by the signal processor 220 communicably coupled to the detector 506 and configured to computationally combine the first and second output signals 508a,b in order to determine the characteristic of the sample 202. Again, computationally combining the first and second signals 508a,b may entail determining the ratio of the two signals, such that a ratio of the primary channel A1 against the reference channel A2 is obtained. In some embodiments, the signal processor 220 may be a computer including a non-transitory machine-readable medium, as generally described above.

In at least one embodiment, the device 500 may further include a second detector 510 that may function similarly to the third detector 314 described above with reference to FIG. 3a, and thereby further provide a second or true reference channel B. In operation, the detector 510 may be arranged to receive and detect optically interacted light 512 in order to generate the compensating signal 318 generally indicative of radiating deviations of the electromagnetic radiation source 201. The compensating signal 318 may be directed to the signal processor 220 and computationally combined with the first and second output signals 310, 312 in order to compensate for any electromagnetic radiating deviations stemming from the electromagnetic radiation source 201.

It should be noted that even though the electromagnetic radiation 204 is shown in FIG. 5 as optically interacting with the sample 202 before reaching the first and second ICE 502, 504, the first and second ICE 502, 504 nonetheless are considered to have optically interacted with the electromagnetic radiation 204, albeit subsequent to the sample 202. In other embodiments, the electromagnetic radiation 204 may optically interact with the first and second ICE 502, 504 before reaching the sample 202, and the sample 202 nonetheless is considered to have optically interacted with the electromagnetic radiation 204, albeit subsequent to the first and second ICE 502, 504. Furthermore, embodiments are contemplated herein where the first ICE 502 is arranged on one side of the sample 202, and the second ICE 504 is arranged on the opposite side of the sample 202. As a result, the electromagnetic radiation 204 may optically interact with the first ICE 502 prior to optically interacting with the sample 202, and subsequently optically interacting with the second ICE 504. It will be appreciated that any and all of the embodiments disclosed herein may include any of the exemplary variations discussed herein, such as arranging the sample 202 before or after the first and second ICE 502, 504, or arranging the ICE 502, 504 in linear or non-linear configurations.

Figure 6:
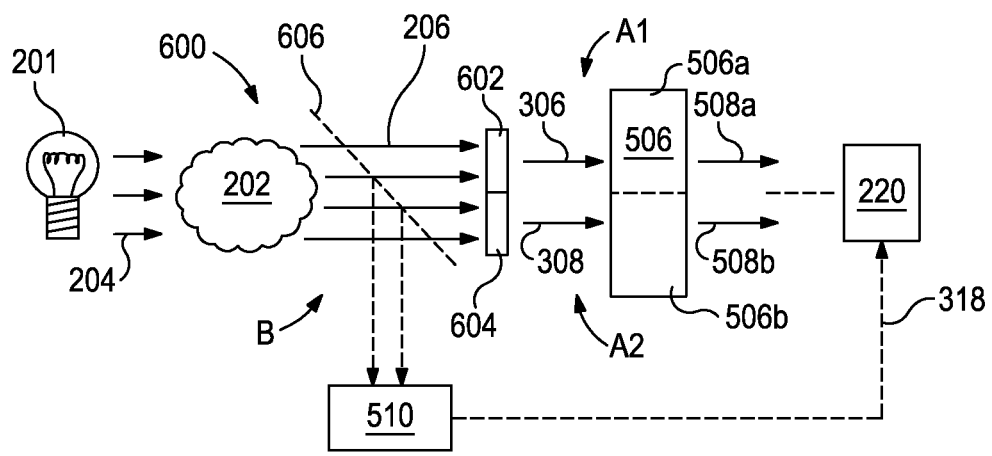
FIG. 6 illustrates another exemplary optical computing device, according to one or more embodiments.

Referring now to FIG. 6, with continued reference to FIG. 5, illustrated is another optical computing device 600, according to one or more embodiments. The device 600 may be somewhat similar to the optical computing device 500 described with reference to FIG. 5, therefore the device 600 may be best understood with reference thereto, where like numerals indicate like elements. The device 600 may include a first ICE 602 and a second ICE 604 similar in construction to the ICE 100 described above with reference to FIG. 1, and configured to be either associated or disassociated with a particular characteristic of the sample 202, such as is described above with reference to the first and second ICE 302, 304 of FIG. 3a.

As illustrated, the first and second ICE 602, 604 may be arranged generally parallel relative to one another and configured to receive the optically interacted light 206. As with prior embodiments, however, the first and second ICE 602, 604 may equally be arranged antecedent to the sample 202, without departing from the scope of the disclosure. In operation, the first ICE 602 may receive a portion of the optically interacted light 206 and thereby generate the first modified electromagnetic radiation 306. The second ICE 604 may be configured to receive another portion of the optically interacted light 206 and thereby generate the second modified electromagnetic radiation 308. As a result, the device 600 may provide a first or primary channel A1 that incorporates the optically interacted light 206 passing through the first ICE 602 and thereafter generating the first modified electromagnetic radiation 306, and a second or reference channel A2 that incorporates the optically interacted light 206 passing through the second ICE 604 and thereafter generating the second modified electromagnetic radiation 308.

The first and second modified electromagnetic radiations 306, 308 may be directed to the detector 506 to generate the first output signal 508a in the primary channel A1 and the second output signal 508b in the reference channel A2 as corresponding to the first and second modified electromagnetic radiations 306, 308, respectively. Specifically, the first detector portion 506a may be configured to receive the first modified electromagnetic radiation 306 and generate the first output signal 508a, and the second detector portion 506b may be configured to receive the second modified electromagnetic radiation 308 and generate the second output signal 508b. In some embodiments, the detector 506 may be configured to computationally combine the first and second output signals 508a,b in order to determine the characteristic of the sample. In other embodiments, however, the first and second signals 508a,b may be received by a signal processor 220 communicably coupled to the detector 506 and configured to computationally combine the first and second signals 508a,b in order to determine the characteristic of the sample.

In some embodiments, the detector 506 is a single detector but configured to time multiplex the first and second modified electromagnetic radiations 306, 308. For example, the first ICE 602 may be configured to direct the first modified electromagnetic radiation 306 toward the detector 506 at a first time T1, and the second ICE 604 may be configured to direct the second modified electromagnetic radiation 308 toward the detector 506 at a second time T2, where the first and second times T1, T2 are distinct time periods that do not spatially overlap. Consequently, the detector 506 receives at least two distinct beams of modified electromagnetic radiation 306, 308 which may be computationally combined by the detector 506 in order to provide an output in the form of a voltage that corresponds to the characteristic of the sample.

In one or more embodiments, in order to provide the first and second times T1, T2, the device 600 may include more than one electromagnetic radiation source 201. In other embodiments, the electromagnetic radiation source 201 may be pulsed in order to provide the first and second times T1, T2. In yet other embodiments, each ICE 602, 604 may be mechanically positioned to interact with the electromagnetic radiation beam at two distinct times. In yet other embodiments, the electromagnetic radiation beam may be deflected, or diffracted to interact with the two different ICE elements at times T1 and T2. Moreover, it will be appreciated that more than the first and second ICE 602, 604 may be used, thereby generating additional primary channels (e.g., A3, A4, . . . An), and the detector 506 may therefore be configured to time multiplex each additional beam of optically interacted light to provide the cumulative voltage corresponding to the characteristic of the sample.

In at least one embodiment, the device 600 may further include the second detector 510 that may function similarly to the third detector 314 described above with reference to FIG. 3a, and thereby further provide a second or true reference channel B. As illustrated, a beam splitter 606 may be arranged to reflect a portion of the optically interacted light 206 toward the second detector 510 in order to generate a compensating signal 318 generally indicative of radiating deviations of the electromagnetic radiation source 201. In other embodiments, however, the second detector 510 may be arranged so as to receive electromagnetic radiation 204 directly from the electromagnetic source 201 or electromagnetic radiation reflected off of either of the ICE 302, 304 and likewise generate the compensating signal 318. The compensating signal 318 may be directed to the signal processor 220 and computationally combined with the first and second output signals 310, 312 in order to compensate for any electromagnetic radiating deviations stemming from the electromagnetic radiation source 201. As a result, a second reference channel B may be included in the device 300 and employed substantially similarly to the reference channel B described above with reference to FIGS. 2a and 2b. In other embodiments, the compensating signal 318 may be used to inform the user of the condition of the electromagnetic radiation source 201, e.g., whether the source 201 is functioning properly.

Figure 7:
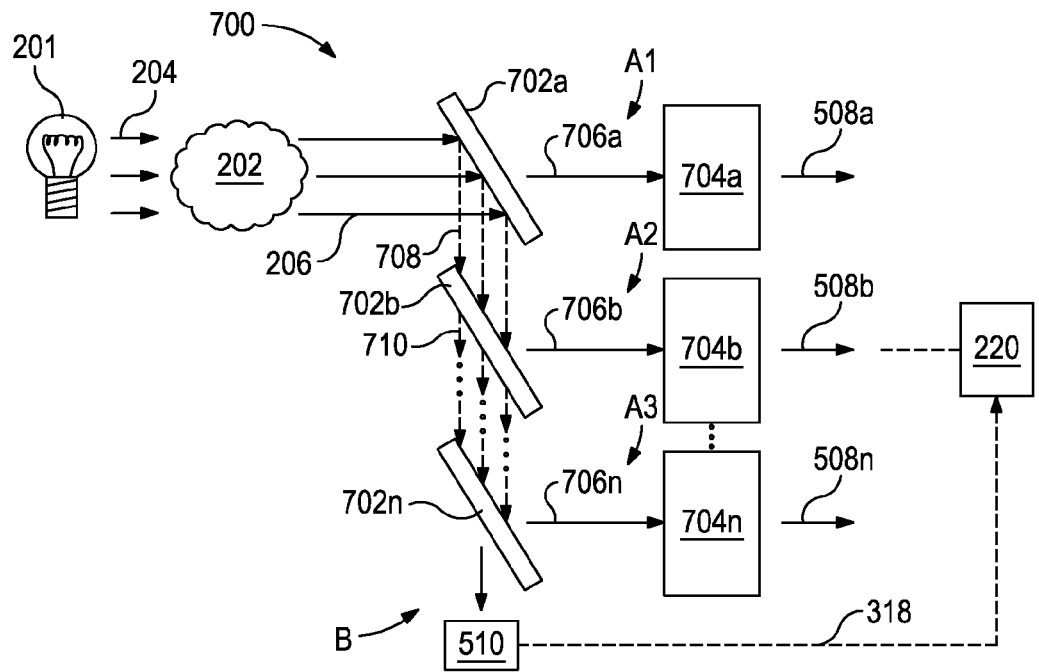
FIG. 7 illustrates another exemplary optical computing device, according to one or more embodiments.

Referring now to FIG. 7, illustrated is another optical computing device 700, according to one or more embodiments. The device 700 may be somewhat similar to the optical computing devices 500, 600 described with reference to FIGS. 5 and 6 and therefore the device 700 may be best understood with reference thereto, where like numerals indicate like elements. The device 700 may include at least two ICE, including a first ICE 702a and a second ICE 702b, but may further include one or more additional ICE 702n. Each ICE 702a-n may be similar in construction to the ICE 100 described above with reference to FIG. 1, and configured to be either associated or disassociated with a particular characteristic of the sample 202, such as is described above with reference to the first and second ICE 302, 304 of FIG. 3a. The device 700 may further include a plurality of detectors, such as a first detector 704a, a second detector 704b, and one or more additional detectors 704n.

The first, second, and additional ICE 702a-n may each be arranged in series relative to one another and configured to optically interact with the electromagnetic radiation 204 either through the sample 202 or through varying configurations of reflection and/or transmission between adjacent ICE 702a-n. In the embodiment specifically depicted, the first ICE 702a may be arranged in a first primary channel A1 to receive the optically interacted radiation 206 from the sample 202. As with prior embodiments, however, the first ICE 702a may equally be arranged antecedent to the sample 202, and therefore optically interact with the electromagnetic radiation 204. The first ICE 702a may be configured to transmit a modified electromagnetic radiation 706a to the first detector 704a and simultaneously convey via reflection optically interacted light 708 toward the second ICE 702b. The second ICE 702b may be arranged in a second primary channel A2 and configured to convey a second optically interacted light 706b via reflection toward the second detector 704b, and simultaneously transmit additional optically interacted light 710 toward the additional ICE 702n.

The additional ICE 702n may be arranged within a reference channel A3, which would otherwise be used to detect radiating deviations of the electromagnetic radiation source 201, but now is used to help determine the characteristic of the sample 202. Accordingly, the reference channel A3 may function substantially similarly to one of the primary channels A1, A2. In operation, the additional ICE 702n may be configured to convey an additional modified electromagnetic radiation 706n via reflection toward the additional detector 704n.

Those skilled in the art will readily recognize numerous alternative configurations of the first, second, and additional ICE 702a-n and corresponding first and second primary channels A1, A2 and the reference channel A3, without departing from the scope of the disclosure. For example, reflection of optically interacted light from a particular ICE may be replaced with transmission of optically interacted light, or alternatively configurations may include the use of mirrors or beam splitters configured to direct the electromagnetic radiation 204 (or optically interacted radiation 206) to each of the first, second, and additional ICE 702a-n.

In at least one embodiment, the device 700 may further include the second detector 510 that may function similarly to the third detector 314 described above with reference to FIG. 3a, and thereby further provide a second or true reference channel B. As illustrated, the detector 510 receives and detects optically interacted light transmitted through the additional ICE 702n and subsequently outputs the compensating signal 318 indicative of electromagnetic radiating deviations. In at least one embodiment, the second detector 510 may be communicably coupled to the signal processor 220 such that the compensating signal 318 may be provided or otherwise conveyed thereto.

The first, second, and additional detectors 704a-n may be configured to detect the first, second, and additional modified electromagnetic radiation 706a-n, respectively, within the corresponding first and second primary channels A1, A2 and the reference channel A3 and thereby generate a first output signal 508a, a second output signal 508b, and one or more additional output signals 508n, respectively. In some embodiments, the first, second, and additional output signals 508a-n may be received by the signal processor 220 communicably coupled to each detector 704a-n and configured to computationally combine the first, second, and additional signals 508a-n in order to determine the characteristic of the sample 202.

This computation may involve a variety of mathematical relationships, including, for example, a linear relationship, a polynomial function, an exponential function, and/or a logarithmic function, or a combination thereof. In these cases, a variety of normalization mathematics between the output signals 508a, 508b . . . 508n and the compensating signal 318 may be applied. For example, the output signals 508a, 508b . . . 508n may each be normalized by dividing them each by the compensating signal 318 to achieve, for example, A1/B, A2/B . . . A3/B, before the mathematical relationship between A1/B and A2/B is applied. In other cases, the mathematical relationship between A1 and A2 may be applied, with the result normalized by B. In even other cases, a combination of these two normalization methods may be applied. Those skilled in the art will be familiar with both general methods, and can choose which method is most applicable given the specific relationships involved. In one embodiment, for example, the compensating signal 318 and the output signals 508a, 508b, . . . 508n are combined using principal component analysis techniques such as, but not limited to, standard partial least squares which are available in most statistical analysis software packages (e.g., XL Stat for MICROSOFT® EXCEL®; the UNSCRAMBLER® from CAMO Software and MATLAB® from MATHWORKS®). Finally, it is understood by those skilled in the art that fractions or multiples of the quantity B may be employed, as well as multiplication of the quantity (1/B).

As will be appreciated, any number of ICE may be arranged within any number of primary channels or otherwise used in series in order to determine the characteristic of the sample 202. In some embodiments, each of the first, second, and additional ICE 702a-n may be specially-designed to detect the particular characteristic of interest or otherwise be configured to be associated therewith. In other embodiments, however, one or more of the first, second, and additional ICE 702a-n may be configured to be disassociated with the particular characteristic of interest, and/or otherwise may be associated with an entirely different characteristic of the sample 202. In yet other embodiments, each of the first, second, and additional ICE 702a-n may be configured to be disassociated with the particular characteristic of interest, and otherwise may be associated with an entirely different characteristic of the sample 202.

Figure 8:
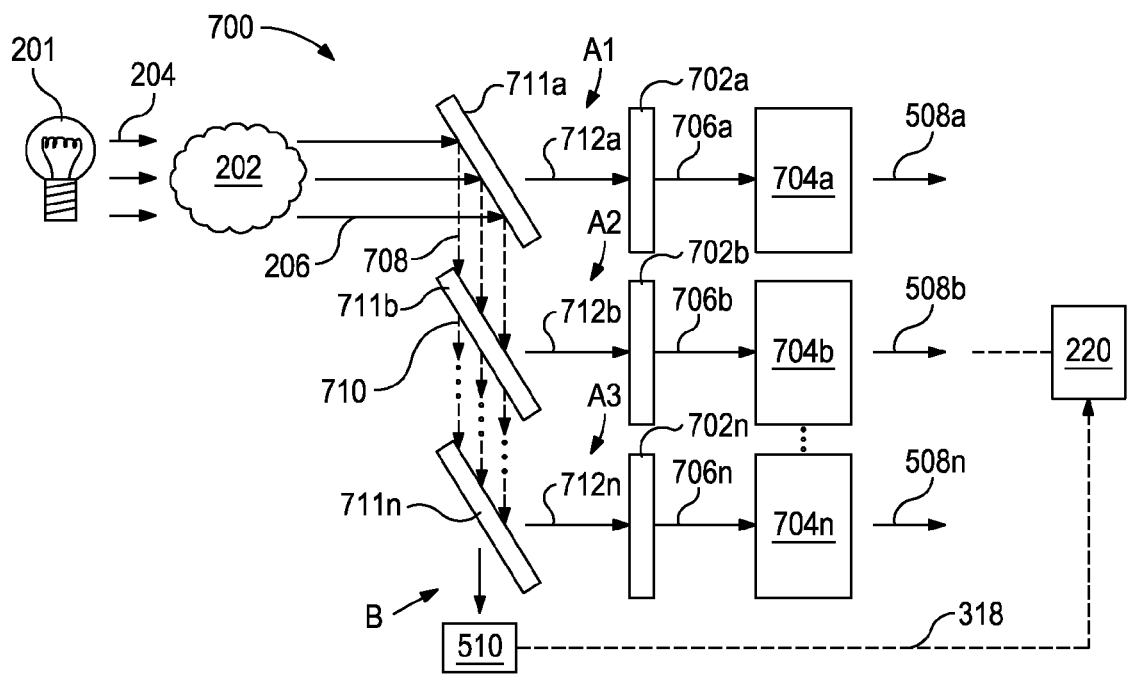
FIGS. 8 and 9 illustrate variations of the optical computing device of FIG. 7, according to one or more embodiments.

Referring now to FIG. 8, illustrated is an alternative configuration of the optical computing device 700, according to one or more embodiments. In FIG. 8, a series of beam splitters 711a, 711b, 711n may be added to the first and second primary channels A1, A2 and the reference channel A3, respectively, and used to separate or otherwise redirect the optically interacted radiation 206 As depicted, each beam splitter 711a-n may be configured to produce and direct a respective beam 712a, 712b, 712n of optically interacted radiation 206 toward a corresponding ICE 702a-n. Each ICE 702a-n may then be configured to transmit its respective modified electromagnetic radiation 706a-n toward a corresponding detector 704a-n, thereby generating the first, second, and additional output signals 508a-n, respectively. The first, second, and additional signals 508a-n may then be received by a signal processor 220 communicably coupled to each detector 704a-n and configured to computationally combine the first, second, and additional signals 508a-n in order to determine the characteristic of the sample 202.

In some embodiments, the second detector 510 may again be used in the second or true reference channel B to detect electromagnetic radiating deviations exhibited by the electromagnetic radiation source 201, and thereby normalize the signals 508a-n produced by the detectors 704a-n. The second detector 510 may be communicably coupled to the signal processor 220 such that the compensating signal 318 indicative of electromagnetic radiating deviations may be provided or otherwise conveyed thereto. The signal processor 220 may then be configured to computationally combine the compensating signal 318 with the signals 508a-n, and thereby normalize the signals 508a-n and provide a more accurate determination of the characteristic of the sample.

Figure 9:
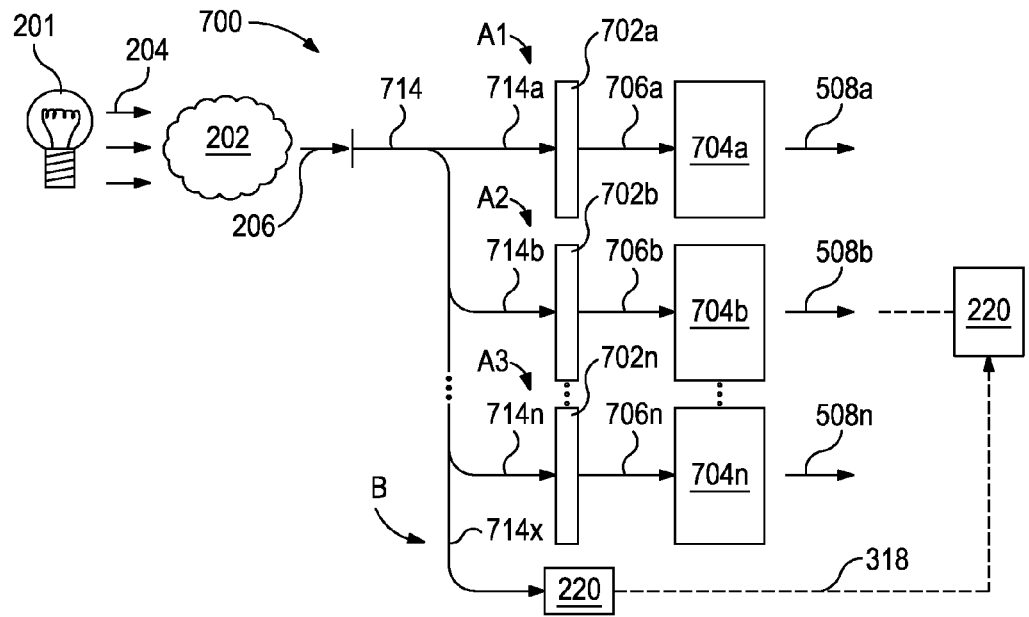

Referring now to FIG. 9, illustrated is yet another alternative configuration of the optical computing device 700, according to one or more embodiments. As illustrated in FIG. 9, the optically interacted radiation 206 may be fed into or otherwise provided to, for example, an optical light pipe 714. The optical light pipe 714 may be configured to convey the optically interacted radiation 206 individually to each of the first and second primary channels A1, A2 and the reference channel A3. In some embodiments, the optical light pipe 714 may be a fiber optic bundle having a plurality of corresponding conveying bundles. In operation, a first bundle 714a may be configured to convey optically interacted radiation 206 to the first ICE 702a in the first primary channel A1 in order to generate the modified electromagnetic radiation 706a; a second bundle 714b may be configured to convey optically interacted radiation 206 to the second ICE 702b in the second primary channel A2 in order to generate the second optically interacted light 706b; and an additional bundle 714n may be configured to convey optically interacted radiation 206 to the additional ICE 702n in the reference channel A3 in order to generate the additional modified electromagnetic radiation 706n. At least one additional bundle 714x may be configured to convey optically interacted radiation 206 to the second detector 510 in the second or true reference channel B in order to generate the compensating signal 318. Processing of the resulting modified electromagnetic radiation 706a-n and signals 508a-n may be accomplished as generally described above.

It should be noted that the use of optical light pipes, such as the optical light pipe 714 discussed above, may be employed in any of the various embodiments and combinations discussed herein, without departing from the scope of the disclosure. Use of a light pipe, or a variation thereof, may prove advantageous in that the light pipe substantially removes interferent obstruction that may otherwise contaminate the optically interacted radiation 206 provided to the various ICEs.

Figure 10:
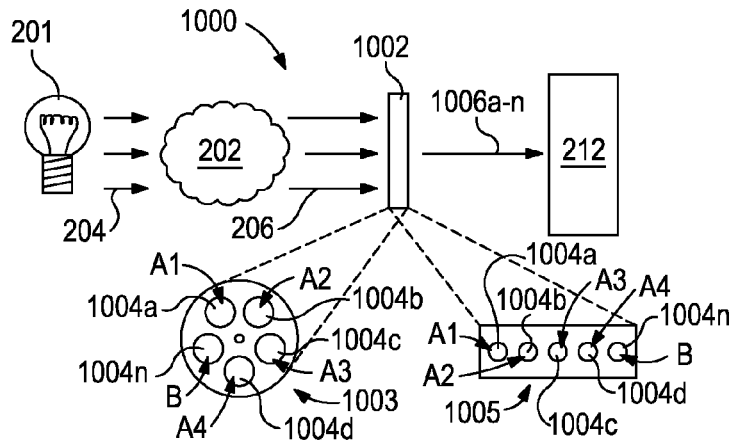
FIG. 10 illustrates another exemplary optical computing device, according to one or more embodiments.

Referring now to FIG. 10, illustrated is another optical computing device 1000, according to one or more embodiments. The device 1000 may be somewhat similar to the optical computing device 300 and 320 described with reference to FIGS. 3a and 3b and therefore the device 1000 may be best understood with reference thereto, where like numerals indicate like elements. The device 1000 may include a movable assembly 1002 having at least two ICEs associated therewith and various corresponding primary channels and at least one reference channel. As illustrated, the movable assembly 1002 may be characterized at least in one embodiment as a rotating disc 1003, wherein the at least two ICEs are radially disposed for rotation therewith. Alternatively, the movable assembly 1002 may be characterized as a linear array 1005, wherein the at least two ICEs are laterally offset from each other. FIG. 10 illustrates corresponding side and frontal views of both the rotating disc 1003 and the linear array 1005, each of which is described in more detail below.

Those skilled in the art will readily recognize, however, that the movable assembly 1002 may be characterized as any type of movable assembly configured to sequentially align at least one detector with optically interacted light 206 and/or one or more ICE. For example, the movable assembly 1002 may include such apparatus or devices as, but not limited to, an oscillating or translating linear array of ICE, one or more scanners, one or more beam deflectors, combinations thereof, or the like. In other embodiments, the movable assembly 1002 may be characterized as an assembly including a plurality of optical light pipes (e.g., fiber optics) configured to perform optical beam splitting to a fixed array of ICE and/or detectors.

Varying embodiments of the rotating disc 1003 may include any number of ICE arranged about or near the periphery of the rotating disc 1003 and circumferentially-spaced from each other. In the illustrated embodiment, the rotating disc 1003 includes a first ICE 1004a, a second ICE 1004b, a third ICE 1004c, and a fourth ICE 1004d, but it will be appreciated that the rotating disc 1003 may also include any number of additional ICE 1004n as needed for the particular application. Each ICE 1004a-n may be similar in construction to the ICE 100 described above with reference to FIG. 1, and configured to be either associated or disassociated with a particular characteristic of the sample 202, such as is described above with reference to the first and second ICE 302, 304 of FIG. 3a. In various embodiments, the rotating disc 1003 may be rotated at a frequency of about 0.1 RPM to about 30,000 RPM.

In operation, the rotating disc 1003 may rotate such that each individual ICE 1004a-n may be exposed to or otherwise optically interact with the optically interacted radiation 206 for a distinct brief period of time. In at least one embodiment, however, the movable assembly 1002 may be arranged antecedent to the sample 202 such that each ICE 1004a-n may be exposed to or otherwise optically interact with the electromagnetic radiation 204 for a brief period of time. Upon optically interacting with the optically interacted radiation 206 each ICE 1004a-n may be configured to produce modified electromagnetic radiation, for example, a first modified electromagnetic radiation 1006a emanating from the first ICE 1004a, a second modified electromagnetic radiation 1006b emanating from the second ICE 1004b, a third modified electromagnetic radiation 1006c emanating from the third ICE 1004c, a fourth modified electromagnetic radiation 1006d emanating from the fourth ICE 1004d, and an additional modified electromagnetic radiation 1006n emanating from the one or more additional ICE 1004n.

As each individual ICE 1004a-n aligns with the optically interacted light 206 to produce the modified electromagnetic radiations 1106a-n, respectively, corresponding first, second, third, and fourth primary channels A1, A2, A3, and A4 and one or more reference channels Bn are thereby generated. Since the device 1000 is not necessarily limited to any specific number of ICE 1004a-n, a corresponding number of primary channels may also be defined by the device 1000 (e.g., primary channel(s) An). Moreover, it will be appreciated that, while the rotating disc 1003 may include any number of additional ICE 1004n as needed, any number of corresponding or otherwise unrelated reference channels B may also be included in the device 1000 (e.g., reference channels B1, B2 . . . Bn), without departing from the scope of the disclosure. Whereas at least one of the one or more reference channels B would otherwise be configured to detect radiating deviations of the electromagnetic radiation source 201, embodiments are contemplated herein where a spectrally active additional ICE 1004n is arranged within said reference channel B. As a result, the reference channel B may serve substantially the same purpose as the first, second, third, and fourth primary channels A1, A2, A3, A4 by detecting and determining the characteristic of the sample 202.

In one or more embodiments, however, at least one of the one or more reference channels B (e.g., B1, B2, . . . Bn) may include a neutral spectral element (not shown) configured to simply pass the optically interacted radiation 206 without optical-interaction. As a result, the neutral element may be configured to provide a neutral signal to the detector 212 that may be substantially similar to the compensating signal 318 as described above with reference to FIG. 3a, and thereby generate a true reference channel B, as generally described herein. In operation, the detector 212 may detect the neutral signal which may be indicative of radiating deviations stemming from the electromagnetic radiation source 201.

Each beam of modified electromagnetic radiation 1006a-n may be detected by the detector 212 which may be configured to time multiplex the modified electromagnetic radiation 1006a-n between the individually-detected beams. For example, the first ICE 1004a may be configured to direct the first modified electromagnetic radiation 1006a toward the detector 212 at a first time T1, the second ICE 1004b may be configured to direct the second modified electromagnetic radiation 1006b toward the detector 212 at a second time T2, and so on until the one or more additional ICE 1004n may be configured to direct the additional modified electromagnetic radiation 1006 toward the detector 212 at an additional time Tn. Consequently, the detector 212 receives a plurality of distinct beams of modified electromagnetic radiation 1006a-n which may be computationally combined by the detector 212 in order to provide an output in the form of a voltage that corresponds to the characteristic of the sample. In some embodiments, these beams of modified electromagnetic radiation 1006a-n may be averaged over an appropriate time domain (e.g., about 1 millisecond to about 1 hour) to more accurately determine the characteristic of the sample 202.

The time multiplexed computation from the various primary channels A1, A2, . . . An and reference channel(s) B (e.g., B1, B2, . . . Bn) may involve a variety of mathematical relationships, including, for example, a linear relationship, a polynomial function, an exponential function, and or a logarithmic function, or a combination thereof. In these cases, a variety of normalization mathematics between the primary channels A1, A2, . . . An and reference channel(s) B may be applied. For example, the signals A1, A2, . . . An may each be normalized by dividing them each by B1, B2, . . . Bn (or a mathematical combination of B1, B2, . . . Bn) to achieve, for example, A1/B, A2/B . . . An/B, before the mathematical relationship between A1/B and A2/B is applied. In other cases, the mathematical relationship between A1, A2, . . . An may be applied, with the resultant normalized by B1, B2 . . . Bn (or a mathematical combination of B1, B2 . . . Bn). In even other cases, a combination of these two normalization methods may be applied. Those skilled in the art will be familiar with both general methods, and can choose which method is most applicable given the specific relationships involved. In one embodiment, for example, the compensating signal B1, B2 . . . Bn and the output signals A1, A2 . . . An are combined using principal component analysis techniques such as, but not limited to, standard partial least squares which are available in most statistical analysis software packages (e.g., XL Stat for MICROSOFT® EXCEL®; the UNSCRAMBLER® from CAMO Software and MATLAB® from MATH-WORKS®). Finally, it is understood by those skilled in the art that fractions or multiples of the quantity B may be employed, as well as multiplication of the quantity (1/B).

As will be appreciated, each of the ICE 1004a-n may be specially-designed to detect or otherwise configured to be associated with the particular characteristic of interest. In other embodiments, however, one or more of the ICE 1004a-n may be configured to be disassociated with the particular characteristic of interest, and otherwise may be associated with an entirely different characteristic of the sample 202. In yet other embodiments, each of the one or more ICE 1004a-n may be configured to be disassociated with the particular characteristic of interest, and otherwise may be associated with an entirely different characteristic of the sample 202. Advantages of this approach can include the ability to analyze multiple analytes in multiple respective channels using a single optical computing device and the opportunity to assay additional analytes simply by adding additional ICEs to the rotating disc 1003.

The linear array 1005 may also include the first, second, third, and fourth ICE 1004a-d and the one or more additional ICE 1004n, although aligned linearly as opposed to radially positioned. The linear array 1005 may be configured to oscillate or otherwise translate laterally or vertically such that each ICE 1004a-n is exposed to or otherwise able to optically interact with the optically interacted radiation 206 for a distinct brief period of time. Similar to the rotating disc 1003, the linear array 1005 may be configured to produce modified electromagnetic radiation 1006a-n. Again, as each individual ICE 1004a-n aligns with the optically interacted light 206 to produce the modified electromagnetic radiations 1106a-n, respectively, corresponding first, second, third, and fourth primary channels A1, A2, A3, and A4 and one or more reference channels B (e.g., B1, B2, . . . Bn) are thereby generated. As will be appreciated, any number of ICE 1004a-n may be arranged on the linear array 1005 in order to determine the characteristic of the sample 202, and therefore any number of corresponding primary channels A1-A4 and additional reference channels B may also be generated.

Moreover, as with the rotating disc 1003 embodiment, the detector 212 may be configured to time multiplex the modified electromagnetic radiation 1006a-n between the individually-detected beams and subsequently provide an output in the form of a voltage that corresponds to the characteristic of the sample 202. Even further, at least one of the ICE 1004a-n may be a neutral element configured to provide a neutral signal to the detector 212 in a true reference channel B that may be computationally combined with the remaining beams of modified electromagnetic radiation 1006a-n to compensate for electromagnetic radiating deviations stemming from the electromagnetic radiation source 201.

Figure 11:
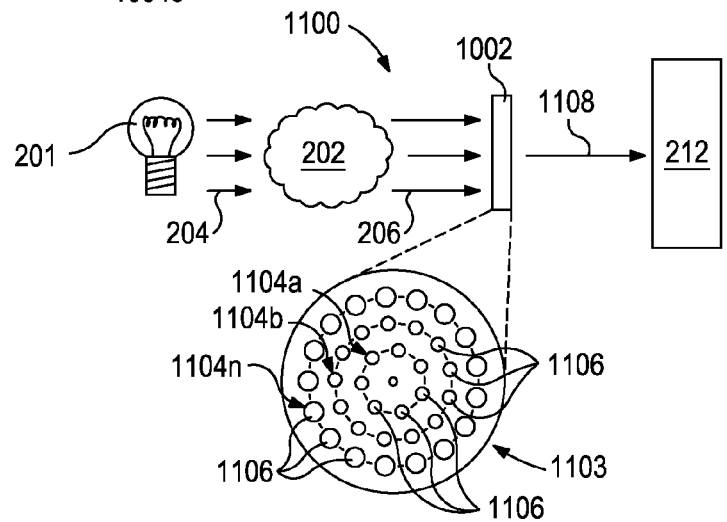
FIG. 11 illustrates another exemplary optical computing device, according to one or more embodiments.

Referring now to FIG. 11, with continued reference to FIG. 10, illustrated is another exemplary optical computing device 1100, according to one or more embodiments. The device 1100 may be somewhat similar to the device 1000 of FIG. 10, and therefore may be best understood with reference thereto where like numerals indicate like elements. The device 1100 may include a movable assembly 1102 similar in some respects to the movable assembly 1002 of FIG. 10. For example, FIG. 11 illustrates an alternative embodiment of a rotating disc 1103. The rotating disc 1103 in FIG. 11, however, may include multiple radially-offset rows or arrays of ICE, such as a first radial array 1104a, a second radial array 1104b, and one or more additional radial arrays 1104n. Accordingly, while three radial arrays 1104a, 1104b, and 1104n are shown in FIG. 11, it will be appreciated that the rotating disc 1103 may include more or less than three arrays 1104a-n, without departing from the scope of the disclosure.

Each radially-offset radial array 1104a-n may include a plurality of ICE 1106 circumferentially-spaced from each other. Again, while a particular number of ICE 1106 are specifically depicted in FIG. 11, it should be appreciated that any number of ICE 1106 may be used in the rotating disc 1103, without departing from the scope of the disclosure. Each ICE 1106 may be similar in construction to the ICE 100 described above with reference to FIG. 1, and configured to be either associated or disassociated with a particular characteristic of the sample 202, such as is described above with reference to the first and second ICE 302, 304 of FIG. 3a. In operation, the rotating disc 1103 rotates such that the one or more ICE 1106 may each be exposed to or otherwise optically interact with the optically interacted radiation 206 for a distinct brief period of time. In at least one embodiment, however, the rotating disc 1103 may be arranged antecedent to the sample 202, and therefore the one or more ICE 1106 may be exposed to or otherwise optically interact with the electromagnetic radiation 204 for a brief period of time. Upon optically interacting with the optically interacted radiation 206, each ICE 1106 may be configured to produce an individual or combined beam of modified electromagnetic radiation 1008 directed toward the detector 212. Moreover, as each individual ICE 1106 aligns with the optically interacted light 206 to produce corresponding modified electromagnetic radiations 1008, several distinct primary channels for conveying and detecting light are generated, and at least one reference channel is generated that may operate substantially similarly to a primary channel since an ICE 1106 is arranged therein as opposed to a traditional neutral element.

Each individual or combined beam of modified electromagnetic radiation 1008 may be detected by the detector 212 which may be configured to time multiplex the modified electromagnetic radiation 1008 between the combined or individually-detected beams in each primary and reference channel. Consequently, the detector 212 receives a plurality of beams of modified electromagnetic radiation 1008 which may be computationally combined by the detector 212 in order to provide an output in the form of a voltage that corresponds to the characteristic of the sample. Moreover, one or more of the ICE 1106 may be a neutral element or otherwise an aperture may be defined in the rotating disc 1103 and configured to provide a neutral signal to the detector 212, and thereby provide a true reference channel, as generally described above with reference to FIG. 10. The neutral signal may be indicative of radiating deviations stemming from the electromagnetic radiation source 201, and the detector 212 may be configured to computationally combine the neutral signal with the remaining beams of modified electromagnetic radiation 1008 to compensate for electromagnetic radiating deviations stemming from the electromagnetic radiation source 201, and thereby provide a more accurate determination of the characteristic of the sample.

While the various embodiments disclosed herein provide that the electromagnetic radiation source 201 is used to provide electromagnetic radiation that optically interacts with the at least two ICEs, those skilled in the art will readily recognize that electromagnetic radiation may be derived from the sample 202 itself, and otherwise derived independent of the electromagnetic radiation source 201. For example, various substances naturally radiate electromagnetic radiation that is able to optically interact with the at least two ICEs. In some embodiments, the sample 202 may be a blackbody radiating substance configured to radiate heat that may optically interact with the at least two ICEs. In other embodiments, the sample 202 may be radioactive or chemo-luminescent and therefore radiate electromagnetic radiation that is able to optically interact with the at least two ICEs. In yet other embodiments, the electromagnetic radiation may be induced from the sample 202 by being acted upon mechanically, magnetically, electrically, combinations thereof, or the like. For instance, in at least one embodiment a voltage may be placed across the sample 202 in order to induce the electromagnetic radiation. As a result, embodiments are contemplated herein where the electromagnetic radiation source 201 is entirely omitted from the particular optical computing device.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A device, comprising:
    an electromagnetic radiation source configured to optically interact with a sample having a characteristic of interest;
    a first integrated computational element arranged within a primary channel and configured to optically interact with the electromagnetic radiation source and produce a first modified electromagnetic radiation;
    a second integrated computational element arranged within a reference channel and configured to optically interact with the electromagnetic radiation source and produce a second modified electromagnetic radiation; and
    a first detector arranged to generate a first signal from the first modified electromagnetic radiation, to generate a compensating signal from the second modified electromagnetic radiation, the compensating signal indicative of a radiating deviation in the primary channel, and to generate an output signal corresponding to the characteristic of the sample.

2. The device of claim 1, wherein the first detector is a split detector comprising a first detector portion arranged in the primary channel to receive the first modified electromagnetic radiation and a second detector portion arranged in the reference channel to receive the second modified electromagnetic radiation.

3. The device of claim 2, wherein the split detector computationally combines the first and second modified electromagnetic radiations to determine the characteristic of the sample.

4. The device of claim 2, wherein the output signal comprises a first output signal generated by the first detector portion and a second output signal generated by the second detector portion, the first and second output signals being transmitted to and received by a signal processor configured to computationally combine the first and second output signals to determine the characteristic of the sample.

5. The device of claim 1, further comprising a second detector arranged in a second reference channel and configured to detect electromagnetic radiating deviations stemming from the electromagnetic radiation source.

6. The device of claim 1, further comprising a signal processor communicably coupled to the first detector, the signal processor being configured to receive and computationally combine the output signal and the compensation signal to normalize the output signal.

7. The device of claim 1, wherein the first and second integrated computational elements are coupled together to form a monolithic structure.

8. The device of claim 1, wherein the first and second computational elements are arranged in series.

9. The device of claim 1, wherein the first and second integrated computational elements are arranged parallel relative to the other.

10. The device of claim 1, wherein the first and second integrated computational elements are configured to be associated with the characteristic of the sample.

11. The device of claim 1, wherein at least one of the first and second integrated computational elements is configured to be disassociated with the characteristic of the sample.

12. The device of claim 1, further comprising a movable assembly configured for rotation, the first and second integrated computational elements being radially disposed within the movable assembly for rotation therewith,
    wherein the primary channel is generated as the first integrated computational element aligns with the electromagnetic radiation source and the first detector, and the reference channel is generated as the second integrated computational element aligns with the electromagnetic radiation source and the first detector.

13. The device of claim 1, wherein the first and second integrated computational elements are laterally arranged upon a movable assembly such that the first and second integrated computational elements optically interact with electromagnetic radiation individually,
    wherein the primary channel is generated as the first integrated computational element aligns with the electromagnetic radiation source and the first detector, and the reference channel is generated as the second integrated computational element aligns with the electromagnetic radiation source and the first detector.

14. The device of claim 13, wherein the movable assembly is configured for lateral or vertical oscillation.

15. A device, comprising:
    an electromagnetic radiation source configured to optically interact with a sample having a characteristic of interest;
    a first integrated computational element arranged within a primary channel and configured to optically interact with the electromagnetic radiation source and produce a first modified electromagnetic radiation;
    a second integrated computational element arranged within a second channel and configured to optically interact with the electromagnetic radiation source and produce a second modified electromagnetic radiation;
    a first detector arranged to receive the first modified electromagnetic radiation and generate a first output signal;
    a second detector arranged to receive the second modified electromagnetic radiation and generate a second output signal; and
    a signal processor configured to receive and computationally combine the first and second output signals to determine the characteristic of interest of the sample, wherein the second output signal is a compensating signal indicative of a radiating deviation in the primary channel.

16. The device of claim 15, further comprising a beam splitter configured to produce a first beam of light directed toward the first integrated computational element and a second beam of light directed toward the second integrated computational element.

17. The device of claim 15, wherein the second detector is arranged in a second reference channel and is further configured to detect electromagnetic radiating deviations from the electromagnetic radiation source.

18. The device of claim 15, wherein the signal processor is configured to receive and computationally combine the output signal and the compensation signal to normalize the output signal.

19. The device of claim 15, wherein the first and second integrated computational elements are coupled together to form a monolithic structure.

20. The device of claim 15, wherein the first and second computational elements are arranged in series.

21. The device of claim 15, wherein the first and second integrated computational elements are arranged parallel relative to the other.

22. The device of claim 15, wherein the first and second integrated computational elements are configured to be associated with the characteristic of the sample.

23. The device of claim 15, wherein at least one of the first and second integrated computational elements is configured to be disassociated with the characteristic of the sample.

\* \* \* \* \*